United States Patent [19]
Balkovec et al.

[11] Patent Number: 5,948,770
[45] Date of Patent: Sep. 7, 1999

[54] ANTIFUNGAL MACROLIDES AND THEIR SYNTHESIS

[75] Inventors: James M. Balkovec, North Plainfield; Bruno Tse, Edison, both of N.J.

[73] Assignee: Merck & Co., Inc., Rahway, N.J.

[21] Appl. No.: 09/009,825

[22] Filed: Jan. 20, 1998

Related U.S. Application Data

[60] Provisional application No. 60/036,470, Jan. 28, 1997.

[51] Int. Cl.$^6$ .......................... A61K 31/33; C07D 313/00
[52] U.S. Cl. .......................... 514/183; 514/450; 540/145; 549/266; 549/271
[58] Field of Search ...................................... 549/266, 271; 540/145; 514/183, 450

[56] References Cited

FOREIGN PATENT DOCUMENTS 1667724  5/1992  Japan .
1667737  5/1992  Japan .

OTHER PUBLICATIONS

Annals of the NY Academy of Sciences, vol. 544, pp. 128–140 (1988), by H. Achenbach, et al.
J. of Antibiotics, vol. XXXIX, No. 12, pp. 1760–1764 (1986).
J. of Antibiotics, vol. XXXVIII, No. 12, pp. 1806–1809, 1810–1812 (1985).
J. of Antibiotics, vol. XXXIX, No. 7, pp. 1016–1020 (1986).
Achenbach et al., Tetrahedron Letters, 26(50) p. 6167–70, 1985.

*Primary Examiner*—Johann Richter
*Assistant Examiner*—Taofiq A. Solola
*Attorney, Agent, or Firm*—Elliott Korsen; Mark Daniel

[57] ABSTRACT

There are disclosed novel antifungal macrolides of the formula

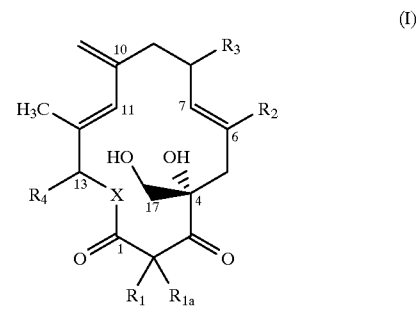

(I)

compositions containing said compounds, methods of using said compounds and a method for synthesizing the compounds.

5 Claims, No Drawings

ANTIFUNGAL MACROLIDES AND THEIR SYNTHESIS

This Appl. claims the benefit of Provisional Appl. filed No. 60/036,470 filed Jan. 28, 1997.

BACKGROUND OF THE INVENTION

Galbonolide A (Rustmicin) and Galbonolide B were independently reported in 1985 by Takatoni et al., J. Antibiotics 38, 1807–1809 and Achenbach et al., J. Antibiotics 39, 1760–1764. Galbonolide B was originally isolated as a fungal metabolite from *Micromonospora chalcea* by Otake and from *Streptomyces galbus* by Achenbach, independently. The compounds exhibit antifungal activity against a number of fungi including Candida, Fusarium, Rhodotorula and Cryptococcus that are associated with human infections and *Botrytis cinerea* and *Pseudomonas lachrymans* that are harmful to agriculture. Galbonolide A and B have been shown to be especially effective against Cryptococcus.

Galbonolide B is claimed in Japanese patent JP 1667737 which issued on May 29, 1992. Galbonolide A is claimed in Japanese patent JP 1667724 which also issued on May 29, 1992. No analogs of Galbonolide A or B have been reported.

SUMMARY OF THE INVENTION

The present invention is directed to novel antifungal macrolides and intermediates useful for their preparation, to methods for their preparation, and to pharmaceutical compositions containing said compounds for use in mammals. It is also directed to compositions containing said compounds for use against plant fungal pathogens.

There are disclosed compounds of the formula

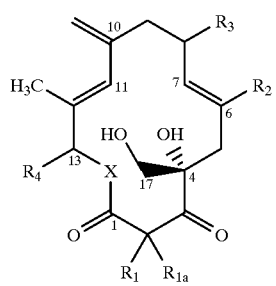

(I)

wherein $R_1$ is H or $C_1$–$C_6$ alkyl;
$R_{1a}$ is H or $C_1$–$C_6$ alkyl;
$R_2$ is H, $C_1$–$C_6$ alkyl or $C_1$–$C_6$ alkoxy;
$R_3$ is H or $C_1$–$C_6$ alkyl;
$R_4$ is H or $C_1$–$C_6$ alkyl;
X is O or NH;
with the proviso that if $R_1$ and $R_3$ are methyl and $R_{1a}$ is hydrogen, $R_4$ is ethyl and $R_2$ is methyl or methoxy, X cannot be O,
or a pharmaceutically acceptable addition salt and/or hydrate thereof, or where applicable, a geometric or optical isomer or racemic mixture thereof.

The invention is also directed to a novel synthesis of these compounds that does not require the natural product as a starting material.

A further aspect of the invention is pharmaceutical compositions containing said compounds in combination with a pharmaceutically acceptable carrier. The invention also relates to antifungal compositions containing an antifungally effective amount of said compounds in admixture with a biologically inert carrier.

A still further aspect of the invention is a method of using the compounds as antifungal agents against both human and plant fungal pathogens.

DETAILED DESCRIPTION OF THE INVENTION

The present invention relates to compounds of the general formula

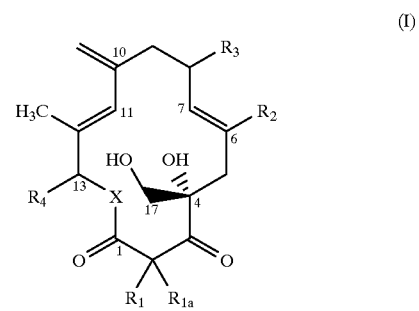

(I)

wherein $R_1$ is H or $C_1$–$C_6$ alkyl;
$R_{1a}$ is H or $C_1$–$C_6$ alkyl;
$R_2$ is H, $C_1$–$C_6$ alkyl or $C_1$–$C_6$ alkoxy;
$R_3$ is H or $C_1$–$C_6$ alkyl;
$R_4$ is H or $C_1$–$C_6$ alkyl;
X is O or NH;

with the proviso that if $R_1$ and $R_3$ are methyl and $R_{1a}$ is hydrogen, $R_4$ is ethyl and $R_2$ is methyl or methoxy, X cannot be O, or a pharmaceutically acceptable addition salt and/or hydrate thereof, or where applicable, a geometric or optical isomer or racemic mixture thereof.

There are also disclosed novel intermediates (II–V) useful in the preparation of the above compounds of the formula:

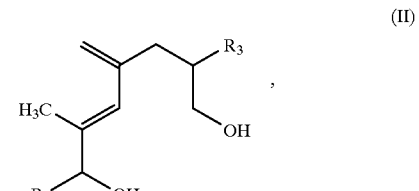

(II)

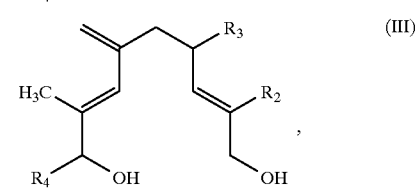

(III)

-continued

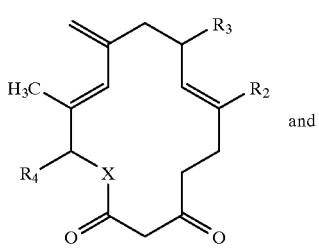
(IV)

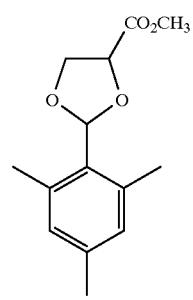
(V)

where all substituents are as defined above.

Unless otherwise stated or indicated, the following definitions shall apply throughout the specification and claims.

When any variable occurs more than one time in any constituent or in formula I, its definition on each occurrence is independent of its definition at every other occurrence. Also, combinations of substituents and/or variables are permissible only if such combinations result in stable compounds.

The term "alkyl" is intended to include both branched-and straight-chain saturated aliphatic hydrocarbon groups having the specified number of carbon atoms, e.g., methyl (Me), ethyl (Et), propyl, butyl, pentyl, hexyl, heptyl, octyl, nonanyl, decyl, undecyl, dodecyl, and the isomers thereof such as isopropyl (i-Pr), isobutyl (i-Bu), sec-butyl (s-Bu), tert-butyl (t-Bu), isopentane, isohexane, etc.

Galbonolide B is a highly unstable natural product. In order to prepare analogs, it was necessary to develop a total synthesis. Generally, the compounds are prepared according to the following series of steps:

Compound VI of the formula

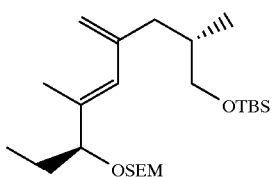
(VI)

which is prepared as described hereinafter is reacted with Compound V of the formula

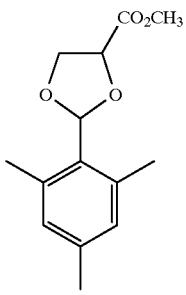
(V)

to afford Compound VII of the formula

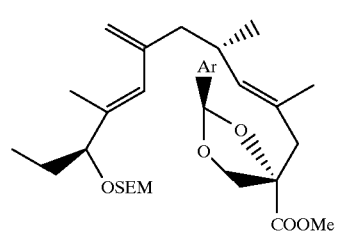
(VII)

Compound VII is subsequently converted to Compound VIII of the formula

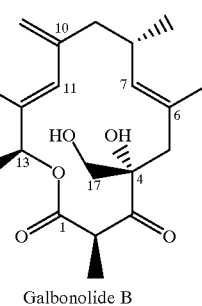
(VIII)

which is reacted to form Compound IX, Galbonolide B, or analogs thereof.

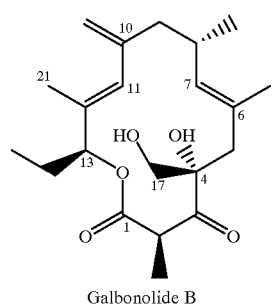
(IX)

Galbonolide B

The complete synthesis of Galbonolide B is shown below in the following reaction schemes:

Scheme 1
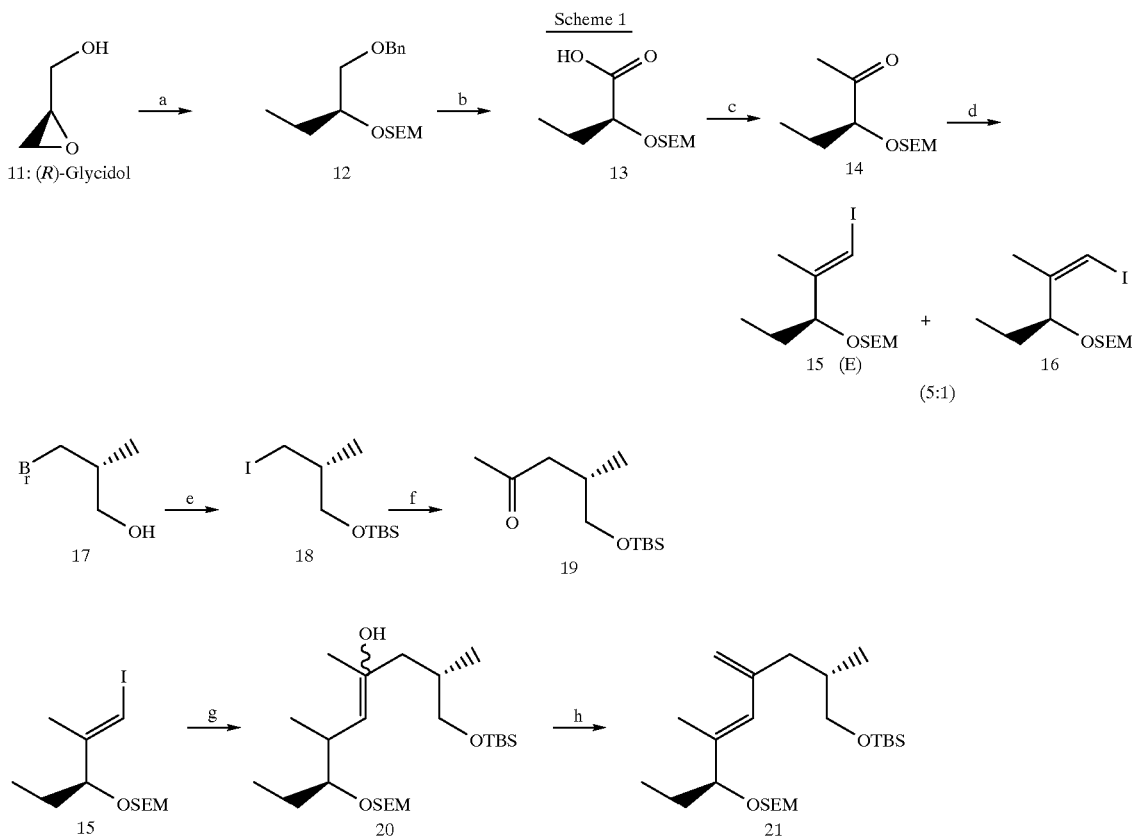
Reagents and Conditions: a. 1. BnBR, NaH, DMF, rt. 2. MeMgI, CuI, THF, -78° C.
3. SEMCl, i-Pr₂NEt, CH₂Cl₂, rt. b. 1.H₂ (balloon), Pd(OH)₂ on C, THF—MeOH. 2. PDC, DMF, rt.
c. MeMgCl, ether, 0°C. d. CHI₃, CrCl₂, THF, 0°C. e. 1. TSOTf, i-Pr₂NEt, CH₂Cl₂, -78° C.
2. LiI, THF, reflux. f. Ethyl vinyl ether, t-BuLi, THF, rt, followed by acid work-up.
g. 1. t-BuLi, ether, -78°C. 2. Methyl ketone 19, THF-ether, -78° C.
h. Martin's sulfurane reagent, CH₂Cl₂, rt.

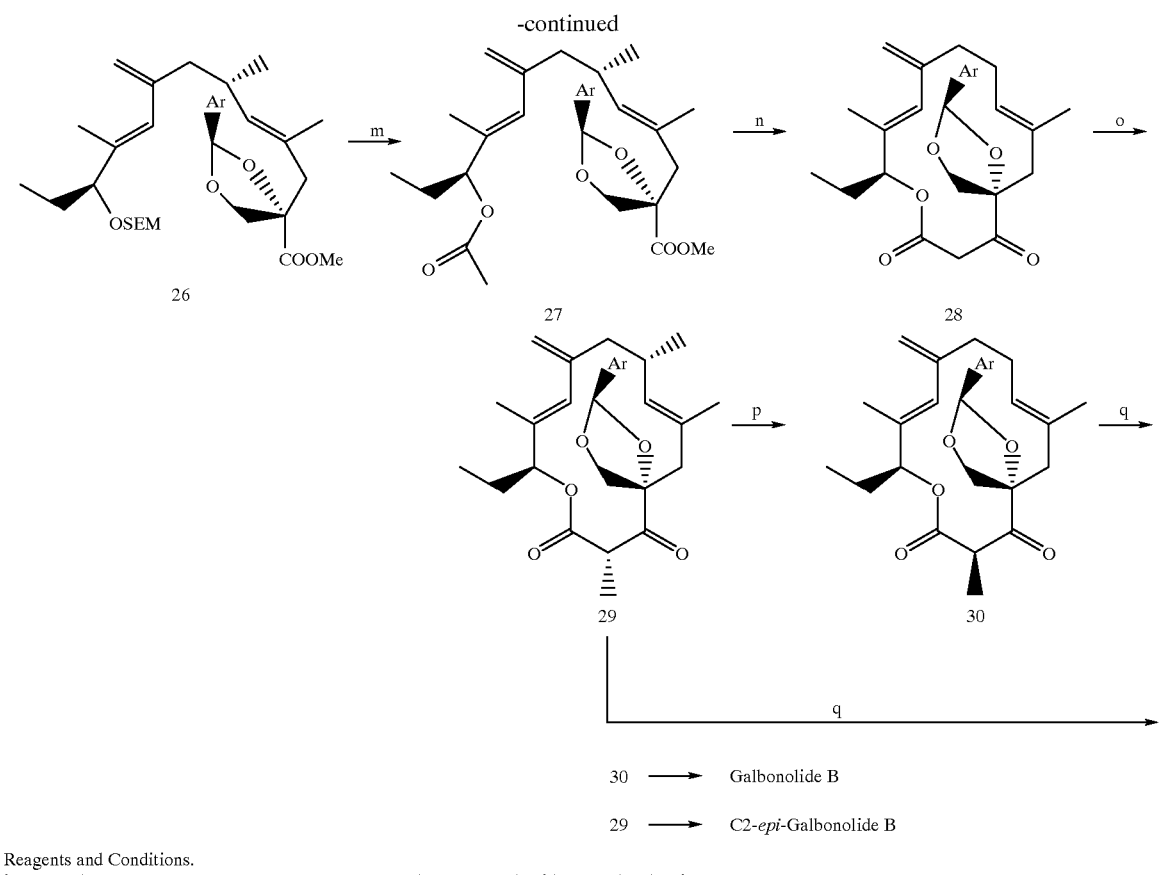

Reagents and Conditions.
i. 1. *p*-Tsoh, MeOH—H$_2$O, rt. 2. ArCHO, CSA, CHCl$_3$, Dean-Stark with 4A molecular sieves.
j. 1. Et$_4$NF, DMF, rt. 2. (COCl)$_2$, DMSO, NEt$_3$, CH$_2$Cl$_2$, -78° C. 3. (EtO)$_2$POCHMeCOOEt (31), LiCl, DBU, CH$_3$CN, 0° C.
k. 1. DIBAL—H, CH$_2$Cl$_2$, -78° C. 2. PPh$_3$, imidazole, I$_2$, ether-CH$_3$CN, -30° C.
l. Acetal 23 , LiHMDS,THF—HMPA, -78° C.
m. 1. Et$_4$NF, DMSO, powdered 4A molecular sieves, 90° C. 2. CH$_2$N$_2$, ether, rt. 3. Ac$_2$O, pyridine, DMAP, rt.
n. LiHMDS, THF, high-dilution, reflux.
o. 1. KO*t*-Bu, DMF, 0°C. 2. MeI.
p. 1. KO*t*-Bu, DMF, 0°C. 2. AcOH quench. q.AcOH—H$_2$O  (2:1 by volume), rt.

As shown in Scheme 2, the total synthesis leading to Galbonolide B or analogs thereof required the selection of the proper starting materials.

Scheme 2

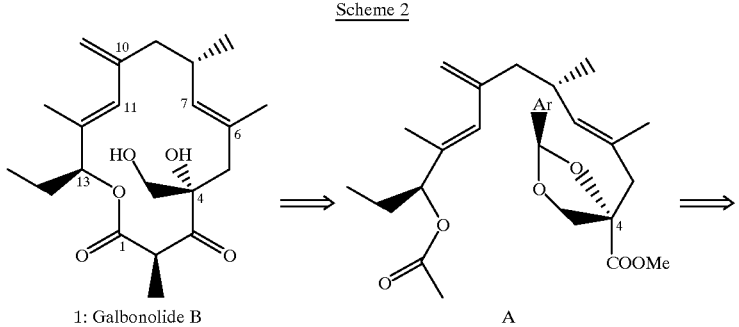

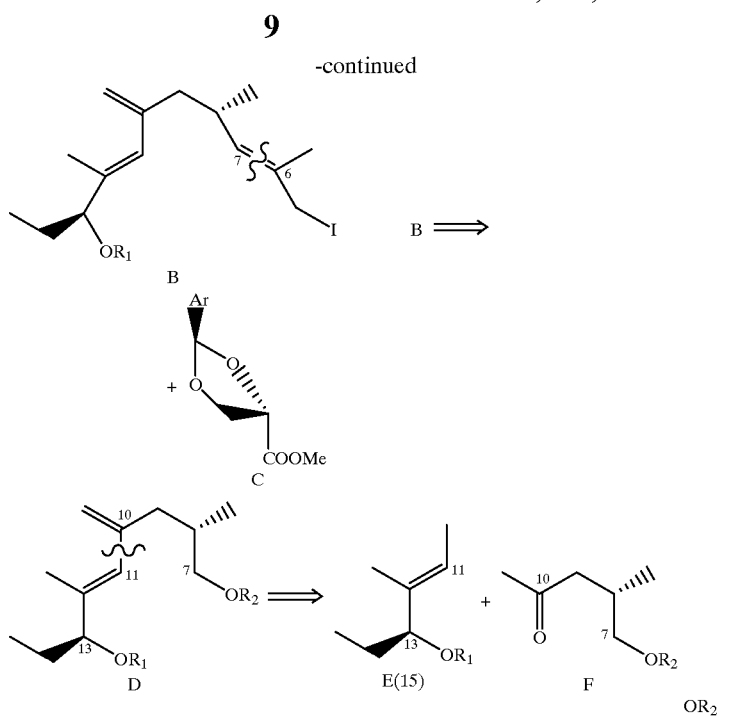

Total Synthesis

Retrosynthetically, to assemble the β-keto lactone moiety in a 14-membered ring, a novel macro-Dieckmann cyclization was planned on A. The proper configuration at C4 of A could be achieved from a modification of Seebach's and Ladner's "contra-steric" enolate attack of C on B. The tri-substituted C6–C7 double bond of B could be installed from D through a suitable Wittig or Horner-Emmons' reaction. Noticing the two chiral centers in D were rather distant from each other, it would be intuitive to further disconnect the C10–C11 bond to E and F. This route not only involved simple and efficient assemblies of all carbon-carbon bonds, but also allowed easy access to important analogs of galbonolide B through simple modifications.

Fragments E and F were obtained from readily available chiral starting materials. (R)-Glycidol (11) was chosen as the starting material for E. After benzylation, the epoxide was selectively opened at the primary center by MeMgI and CuI in THF The secondary alcohol formed was protected as a SEM ether to give Compound 12. Catalytic hydrogenolysis and subsequent PD/C oxidation were employed to furnish the carboxylic acid 13, which reacted with MeMgCl in ether to yield the methyl ketone 14. Employing the procedure of Takai, J. Am. Chem. Soc. (1986), 108, 7408, upon reaction with $CHI_3$ and $CrCl_2$ in THF, Compound 14 was converted to the desired vinyl iodide 15 and the undesired isomer 16 in 5:1 ratio. The two vinyl iodides were separable by silica gel chromatography.

To prepare Fragment F, the commercially available (R)-3-bromo-2-methyl-1-propanol (17) was used as the starting material. After protection of the alcohol as a TBS ether (18), the bromide was displaced by iodide to function as a better leaving group. The umpolung, lithiated ethyl vinyl ether, was used to displace the iodide. After acid work-up, the desired methyl ketone 19 was obtained.

For the coupling of Compounds 15 and 19, Li-I exchange was first performed on 15 with tert-butyllithium in ether. The vinyl-lithium species formed was then trapped with 19 to give diastereomeric 20. Upon the screening of a number of dehydrating conditions, Martin's sulfurane reagent worked best and most efficiently to give the desired diene 21 in high yield and high selectivity.

After selective removal of the TBS group in 21 with $Et_4NF$ in DMF in the presence of the SEM ether, the resultant alcohol as oxidized to the corresponding aldehyde by a standard Swern oxidation. To install the C6–C7 trisubstituted double bond, a Horner-Emmon's reaction using the phosphonate 31 was employed. Among all the conditions attempted, the Roush-Masamune conditions using LiCl, DBU in $CH_3CN$ performed best to give the desired E alkene 24 as the only isomer observed. The ethyl ester was subsequently reduced by DIBAL-H to the alcohol 32, which was then converted to the iodo compound 25 by $PPh_3$, imidazole and $I_2$.

To prepare for the next step, the commercially available acetonide 22 was first hydrolyzed to give the corresponding diol, which was then treated with an aromatic aldehyde to give Compound 23. A modification of Seebach's and Ladner's "contra-steric" enolate chemistry was then carried out on Compound 25. Upon treatment of 23 with LiHMDS in a THF/HMPA solvent system, the lithium enolate reacted with 25 to furnish compound 26. The SEM ether was then cleaved by $Et_4NF$ in DMSO at 90° C. in the presence of powdered molecular sieves to generate the secondary alcohol at C 13. The methyl ester of Compound 26 was also cleaved in this reaction but it could be regenerated by the reaction of the resultant carboxylic acid with ethereal $CH_2N_2$. Acetylation of the secondary alcohol at C13 furnished compound 27. In order to cyclize the compound, a novel macro-Dieckmann cyclization was carried out. Reaction of Compound 27 with LiHMDS in refluxing THF under high-dilution conditions successfully generated the cyclized product 28. The methyl group at C2 had to be installed after cyclization. To this end, compound 28 was first enolized with KOt-Bu in DMF. Trapping of the enolate with MeI gave Compound 29 as a single isomer, indicating that the nucleophilic attack of the enolate was extremely stereoselective.

Upon the hydrolysis of the 2,4,6-trimethylbenzylidene acetal of Compound 29, the product was found to be identical to C2-epi-galbonolide B, not galbonolide B. The fact that the enolate attack of 28 was very stereoselective suggested that the proton quench of the enolate of 29 could invert the stereochemistry. Indeed, the reaction of 29 with KOt-Bu in DMF, followed by AcOH quench, successfully inverted the stereocenter at C2 to yield Compound 30. Comparing the $^1$H NMR of 29 and 30, notable shifts of signals were observed, which suggested a significant change in the conformation of the macrocycle upon epimerization at C2. The subsequent hydrolysis of the acetal of 30 with AcOH/H$_2$O (2:1) successfully furnished galbonolide B. The synthetic material was identical to the natural product in all aspects, including spectroscopic data, optical rotation and biological activity.

The compounds of the present invention are valuable antifungal agents active against various fungal organisms, and accordingly may be useful in human and veterinary medicine. The compounds of the invention are not limited to utility as medicaments; they may be used in all manner of industry, for example: additives to animal feed, preservation of food, disinfectants, and in other industrial systems where control of fungal growth is desired. For example, they may be employed in compositions in concentrations ranging from about 0.01 to about 100 parts of antibiotic per million parts of solution in order to destroy or inhibit the growth of harmful fungi on medical and dental equipment and as fungicides in industrial applications, for example in water based paints and in the white water of paper mills to inhibit the growth of harmful fungi.

In vitro antifungal activity determined in accordance with the protocol set forth below is predictive of in vivo activity, when the compounds are administered to a mammal infected with a susceptible fungal organism.

The compounds of the present invention are active against many fungi and particularly against Candida, Aspergillus and Cryptococcus species. The antifungal properties may be illustrated with the minimum fungicidal concentration (MFC) determination against certain Candida and Cryptococcus organisms in a microbroth dilution assay carried out in a Yeast Nitrogen Base (Difco) medium with 1 percent dextrose (YNBD).

In a representative assay, a compound of the invention is solubilized in 100 percent dimethyl sulfoxide (DMSO) at an initial concentration of 5 mg/ml. Once dissolved, the drug stock is brought to concentration of 512 mcg/ml by dilution in water such that the final DMSO concentration is about 10 percent. The solution is dispensed via a multichannel pipette into the first column of a 96-well plate (each well containing 0.075 ml of YNBD), resulting in a drug concentration of 256 mcg/ml. Compounds in the first column are diluted 2-fold across the rows yielding final drug concentrations ranging from 256 mcg/ml to 0.12 mcg/ml.

Four hour broth cultures of organisms to be tested are adjusted using a spectrophotometer at 600 nm to equal a 0.5 McFarland Standard. This suspension is diluted 1:100 in YNBD to yield a cell concentration of $1-5\times10^4$ colony forming units (CFU) per ml.

Aliquots of the suspension (0.075 ml) are inoculated into each well of the microtiter plate resulting in a final cell inoculum of $5-25\times10^3$ CFU/ml and final drug concentrations ranging from 128 mcg/ml to 0.06 mcg/ml. Each assay includes one row for drug-free control wells and one row for cell-free control wells.

After 24 hours of incubation, the microtiter plates are gently shaken on a shaker to resuspend the cells. The MIC-2000 inoculator is used to transfer a 1.5 microliter sample from each well of the 96-well microtiter plate to a single reservoir inoculum plate containing Sabouraud dextrose agar (SDA). The inoculated SDA plates are incubated for 24 hours at 35° C. However, for *Cryptococcus neoformans* strains, SDA plates are inoculated at 48 hours after being spotted on SDA before making minimum fungicidal concentration (MFC) readings.

The pharmaceutical compositions containing the active ingredient may be in a form suitable for oral use, for example, as tablets, troches, lozenges, aqueous or oily suspensions, dispersible powders or granules, emulsions, hard or soft capsules, or syrups or elixirs. Compositions intended for oral use may be prepared according to any method known to the art for the manufacture of pharmaceutical compositions and such compositions may contain one or more agents selected from the group consisting of sweetening agents, flavoring gents, coloring agents and preserving agents in order to provide pharmaceutically elegant and palatable preparations. Tablets contain the active ingredient in admixture with non-toxic pharmaceutically acceptable excipients which are suitable for the manufacture of tablets. These excipients may be for example, inert diluents, such as calcium carbonate, sodium carbonate, lactose, calcium phosphate or sodium phosphate; granulating and disintegrating agents, for example, corn starch, or alginic acid; binding agents, for example starch, gelatin or acacia, and lubricating agents, for example, magnesium stearate, stearic acid or talc. The tablets may be uncoated or they may be coated by known techniques to delay disintegration and absorption in the gastrointestinal tract and thereby provide a sustained action over a longer period. For example, a time delay material such as glyceryl monostearate or glyceryl distearate may be employed. They may also be coated by the technique described in the U.S. Pat. Nos. 4,256,108; 4,166,452; and 4,265,874 to form osmotic therapeutic tablets for control release.

Formulations for oral use may also be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example peanut oil, liquid paraffin, or olive oil.

Aqueous suspensions contain the active material in admixture with excipients suitable for the manufacture of aqueous suspensions. Such excipients are suspending agents, for example sodium carboxymethylcellulose, methylcellulose, hydroxypropylmethylcellulose, sodium alginate, polyvinyl-pyrrolidone, gum tragacanth and gum acacia; dispersing or wetting agents may be a naturally-occurring phosphatide, for example lecithin, or condensation products of an alkylene oxide with fatty acids, for example polyoxyethylene stearate, or condensation products of ethylene oxide with long chain aliphatic alcohols, for example heptadecaethylene-oxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives, for example ethyl, or n-propyl, p-hydroxybenzoate, one or more coloring agents, one or more flavoring agents, and one or more sweetening agents, such as sucrose, saccharin or aspartame.

Oily suspensions may be formulated by suspending the active ingredient in a vegetable oil, for example arachis oil, olive oil, sesame oil or coconut oil, or in mineral oil such as liquid paraffin. The oily suspensions may contain a thickening agent, for example beeswax, hard paraffin or cetyl alcohol. Sweetening agents such as those set forth above, and flavoring agents may be added to provide a palatable oral preparation. These compositions may be preserved by the addition of an anti-oxidant such as ascorbic acid.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, for example sweetening, flavoring and coloring agents, may also be present.

The pharmaceutical compositions of the invention may also be in the form of an oil-in-water emulsions. The oily phase may be a vegetable oil, for example olive oil or arachis oil, or a mineral oil, for example liquid paraffin or mixtures of these. Suitable emulsifying agents may be naturally-occurring phosphatides, for example soy beans, lecithin, and esters or partial esters derived from fatty acids and hexitol anhydrides, for example sorbitan monooleate, and condensation products of the said partial esters with ethylene oxide, for example polyoxyethylene sorbitan monooleate. The emulsions may also contain sweetening and flavouring agents.

Syrups and elixirs may be formulated with sweetening agents, for example glycerol, propylene glycol, sorbitol or sucrose. Such formulations may also contain a demulcent, a preservative and flavoring and coloring agents.

The pharmaceutical compositions may be in the form of a sterile injectable aqueous or oleagenous suspension. This suspension may be formulated according to the known art using those suitable dispersing or wetting agents and suspending agents which have been mentioned above. The sterile injectable preparation may also be a sterile injectable solution or suspension in a non-toxic parenterally-acceptable diluent or solvent, for example as a solution in 1,3-butane diol. Among the acceptable vehicles and solvents that may be employed are water, Ringer's solution and isotonic sodium chloride solution. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

Compounds of Formula I may also be administered in the form of a suppositories for rectal administration of the drug. These compositions can be prepared by mixing the drug with a suitable non-irritating excipient which is solid at ordinary temperatures but liquid at the rectal temperature and will therefore melt in the rectum to release the drug. Such materials are cocoa butter and polyethylene glycols.

For topical use, creams, ointments, jellies, solutions or suspensions, etc., containing the compound of Formula I are employed. (For purposes of this application, topical application shall include mouth washes and gargles.)

The compounds for the present invention can be administered in intranasal form via topical use of suitable intranasal vehicles, or via transdermal routes, using those forms of transdermal skin patches well known to those of ordinary skill in the art. To be administered in the form of a transdermal delivery system, the dosage administration will, of course, be continuous rather than intermittent throughout the dosage regimen. Compounds of the present invention may also be delivered as a suppository employing bases such as cocoa butter, glycerinated gelatin, hydrogenated vegetable oils, mixtures of polyethylene glycols of various molecular weights and fatty acid esters of polyethylene glycol.

The dosage regimen utilizing the compounds of the present invention is selected in accordance with a variety of factors including type, species, age, weight, sex and medical condition of the patient; the severity of the condition to be treated; the route of administration; the renal and hepatic function of the patient; and the particular compound thereof employed. A physician or veterinarian of ordinary skill can readily determine and prescribe the effective amount of the drug required to prevent, counter, arrest or reverse the progress of the condition. Optimal precision in achieving concentration of drug within the range that yields efficacy without toxicity requires a regimen based on the kinetics of the drug's availability to target sites. This involves a consideration of the distribution, equilibrium, and elimination of a drug. Preferably, doses of the compound of structural formula I useful in the method of the present invention range from 0.01 to 1000 mg per adult human per day. Most preferably, dosages range from 0.1 to 500 mg/day. For oral administration, the compositions are preferably provided in the form of tablets containing 0.01 to 1000 milligrams of the active ingredient, particularly 0.01, 0.05, 0.1, 0.5, 1.0, 2.5, 5.0, 10.0, 15.0, 25.0, 50.0, 100 and 500 milligrams of the active ingredient for the symptomatic adjustment of the dosage to the patient to be treated. An effective amount of the drug is ordinarily supplied at a dosage level of from about 0.0002 mg/kg to about 50 mg/kg of body weight per day. The range is more particularly from about 0.001 mg/kg to 10 mg/kg of body weight per day.

Advantageously, the active agent of the present invention may be administered in a single daily dose, or the total daily dosage may be administered in dividend doses of two, three or four times daily.

The amount of active ingredient that may be combined with the carrier materials to produce a single dosage form will vary depending upon the host treated and the particular mode of administration.

It will be understood, however, that the specific dose level for any particular patient will depend upon a variety of factors including the age, body weight, general health, sex, diet, time of administration, route of administration, rate of excretion, drug combination and the severity of the particular disease undergoing therapy.

The following examples are for illustrative purposes only and are not to be construed as limiting the invention disclosed herein. Examples 1–23 illustrate the total synthesis of Galbonolide B and Examples 24–34 illustrate the synthesis of analogs of Galbonolide B.

Experimental Section

General. Reactions sensitive to moisture or air were performed under nitrogen using anhydrous solvents and reagents. Reagents and solvents were used as supplied otherwise. $Na_2SO_4$ was used for drying in the aqueous work-ups of reactions. $^1H$ and $^{13}C$ NMR spectra were obtained at 500 and 125 MHz, respectively. Chemical shifts are reported in parts per million, and residual solvent peaks were used as internal references. Coupling constants are reported in hertz. IR spectra were measured as films and the wavenumbers are reported in $cm^{-1}$. Analytical TLC was performed with E. Merck precoated TLC plates, silica gel 60F-254, layer thickness 0.25 mm. Preparative TLC (PTLC) separations were performed on E. Merck precoated TLC plates, silica gel 60F-254, layer thickness 0.50 mm. Flash chromatography was performed with E. Merck Kieselgel 60 (230-400 mesh) silica gel.

EXAMPLE 1

(R)-Glycidol-benzyl ether

To a mixture of (R)-glycidol (25 g, 0.337 mol) and BnBr (60.2 mL, 0.506 mol) in anhydrous DMF (1 L) was slowly added NaH (16.2 g of 60% oil dispersion, 0.405 mol) at 0° C. The mixture was warmed to room temperature and stirred for 3 hours. The mixture was concentrated in vacuo. After aqueous work-up ($CH_2Cl_2$) and chromatography, 44.8 g of the benzyl ether was obtained: $[\alpha]^{25}_D$ −1.6° (c 0.63, $CHCl_3$). $^1$H NMR ($CDCl_3$): δ2.60 (1H, dd, J=2.5, 5.0), 2.79 (1H, dd, J=4.4, 5.0), 3.17 (1H, m), 3.43 ($^1$H, dd, J=5.7, 11.5), 3.75 (1H, dd, J=3.0, 11.5), 4.57 (2H, AB q, J=11.9), 7.32–7.34 (5H, m). $^{13}$C NMR ($CDCl_3$): δ44.3, 50.8, 70.8, 73.3, 127.7, 128.4, 137.8. HRMS (EI) calcd for $C_{10}H_{12}O_2$ 164.0837, found 164.0803.

EXAMPLE 2

(S)-1-Benzyloxy-butan-2-ol

To a mixture of the benzyl ether above (44 g, 0.268 mol) and CuI (51 g, 0.268 mol) in anhydrous THF (1 L) was slowly added MeMgI (270 mL of a 3 M THF solution, 0.810 mol) at −78° C. The mixture was stirred at −78° C. for 4 hours and was warmed to room temperature. After aqueous work-up ($CH_2Cl_2$) and chromatography, 47.0 g of the title compound was obtained: $[\alpha]^{25}_D$+8.2° (c 1.2, $CHCl_3$). IR: 3428. $^1$H NMR ($CDCl_3$): δ0.94 (3H, t, J=7.5), 1.47 (2H, m), 2.38 (1H, br), 3.32 (1H, dd, J=8.0, 9.3), 3.50 (1H, dd, J=2.9, 9.3), 3.73 (1H, m), 4.54 (2H, s), 7.26–7.36 (5H, m). $^{13}$C NMR ($CDCl_3$): δ9.8, 26.1, 71.7, 73.3, 74.3, 127.7, 127.7, 128.4, 138.0. HRMS (EI) calcd for $C_{11}H_{16}O_2$ 180.1150, found 180.1145.

EXAMPLE 3

SEM Ether 12

To a $CH_2Cl_2$ (700 mL) solution of (S)-1-benzyloxy-butan-2-ol (46 g, 0.256 mol) was added i-$Pr_2$NEt (53.4 mL, 0.307 mol) and SEMCl (49.8 mL, 0.281 mol) at 0° C. The mixture was stirred at room temperature overnight. After aqueous work-up ($CH_2Cl_2$) and chromatography, 79.2 g of the title compound was obtained: $[\alpha]^{25}_D$−16.7° (c 1.3, $CHCl_3$). $^1$H NMR ($CDCl_3$): δ−0.01 (9H, s), 0.89 (2H, m), 0.91 (3H; t, J=7.5), 1.50–1.65 (2H, m), 3.48 (2H, m), 3.58–3.70 (3H, m), 4.52 (2H, AB q, J=12.4), 4.75 (2H, AB q, J=7.1), 7.26–7.32 (5H, m). $^{13}$C NMR ($CDCl_3$): δ−1.5, 9.8, 18.1, 24.8, 65.0, 72.3, 73.3, 77.3, 94.1, 127.5, 127.5, 128.3, 138.4.

EXAMPLE 4

Debenzyl-12

To a solution of the compound of Example 3 (79 g, 0.255 mol) in 100 mL of THF and 500 mL of MeOH was added 5 g of Pearlman's catalyst. The mixture was stirred under hydrogen (balloon pressure) for 10 hours with the hydrogen being periodically replenished, and was then filtered through celite. The filtrate was concentrated in vacuo and chromatographed to give 53.6 g of the title compound: $[\alpha]^{25}_D$+38.3° (c 1.0, $CHCl_3$). IR: 3461. $^1$H NMR ($CDCl_3$): δ0.00 (9H, s), 0.91 (3H, t, J=7.6), 0.94 (2H, m), 1.50 (2H, m), 3.42–3.79 (5H, m), 4.67(1H, d, J=7.3),4.80(1H, d, J=7.3). $^{13}$C NMR ($CDCl_3$): δ−1.5, 10.0, 18.1, 24.7, 65.5, 65.7, 84.1, 95.3.

EXAMPLE 5

Methyl ketone 14

To a DMF solution (1 L) of the compound of Example 4, (53 g, 0.241 mol) was added PDC (470 g, 1.25 mol) at 0° C. The mixture was stirred at room temperature for 12 hours. After aqueous work-up (ether) and chromatography (1% AcOH in EtOAc), 42.1 g of the carboxylic acid was obtained, which was used directly in the next step. To a solution of this carboxylic acid (40 g, 0.171 mol) in anhydrous ether (500 mL) was added MeMgI (124 mL of 3M ether solution, 0.372 mol) at 0° C. The mixture was stirred at 0° C. for another 4 hours and then at room temperature overnight. After aqueous work-up ($CH_2Cl_2$) and chromatography, 36.5 g of the title compound was obtained: $[\alpha]^{25}_D$−34.5° (c 0.33, $CHCl_3$). IR: 1718. $^1$H NMR ($CDCl_3$): δ−0.01 (9H, s), 0.89 (2H, m), 0.93 (3H, t, J=7.4), 1.69 (2H, m), 2.14 (3H, s), 3.61 (2H, m), 3.91 (1H, dd, J=5.5, 6.9), 4.67 (2H, AB q, J=7.0). $^{13}$C NMR ($CDCl_3$): δ−1.5, 9.5, 18.0, 25.1, 26.0, 65.8, 83.8, 94.5, 210.1.

EXAMPLE 6

Vinyl iodide 15

To a mixture of the compound of Example 5 (35 g, 0.151 mol) and $CrCl_2$ (111 g, 0.903 mol) in anhydrous THF (750 mL) at 0° C. was added $CHI_3$ (119 g, 0.302 mol). The mixture was stirred at 0° C. for 6 hours and at room temperature overnight. After aqueous work-up (ether) and chromatography, 32.9 g of the title compound and its Z isomer (5:1) were obtained. A small amount was further purified by PTLC to give an analytical sample: $[\alpha]^{25}_D$−92.3° (c 0.29, $CHCl_3$). IR: 1613. $^1$H NMR ($CDCl_3$): δ0.00 (9H, s), 0.85 (3H, t, J=7.4), 0.90 (2H, m), 1.47–1.65 (2H, m), 1.73 (3H, d, J=0.9), 3.45–3.73 (2H, m), 4.01 (1H, t, J=6.9), 4.55 (2H, AB q, J=7.0), 6.2 (1H, s). $^{13}$C NMR ($CDCl_3$): δ−1.4, 10.1, 18.1, 19.0, 26.5, 65.2, 79.4, 81.7, 92.1, 147.3.

EXAMPLE 7

Iodo-compound 18

To a solution of (R)-3-bromo-2-methyl-1-propanol (17) (40.4 g, 0.264 mol) in $CH_2Cl_2$ (500 mL) at −78° C. were added i-$Pr_2$NEt (55.2 mL, 0.317 mol) and TBSOTf (66.7 mL, 0.290 mol). The mixture was stirred at −78° C. for 2 hours and was warmed up to room temperature. After aqueous work-up and chromatography, 70.4 g of the TBS ether was obtained, which was used in the next step directly. To a solution of this TBS ether (70 g, 0.262 mol) in THF (500 mL) was added LiI (281 g, 2.10 mol) at 0° C. The mixture was refluxed overnight and was then concentrated in vacuo. After aqueous work-up ($CH_2Cl_2$) and chromatography, 79.9 g of the title compound was obtained: $[\alpha]^{25}_D$−10.2° (c 0.59, $CHCl_3$). $^1$H NMR ($CDCl_3$): δ0.04 (3H, s), 0.05 (3H, s), 0.88 (9H, s), 0.93 (3H, d, J=6.7), 1.62 (1H, m), 3.23 (1H, dd, J=5.5, 9.4), 3.28 (1H, dd, J=5.1, 9.4), 3.38 (1H, dd, J=6.9, 10.1), 3.50 (1H, dd, J=4.8, 10.1). $^{13}$C NMR ($CDCl_3$): δ−5.4, 13.8, 17.2, 18.3, 25.9, 37.4, 66.7.

EXAMPLE 8

Methyl ketone 19

To a solution of ethyl vinyl ether (131 mL, 1.37 mol) in anhydrous THF (3 L) was added t-BuLi (730 mL of a 1.7 M solution in pentane, 1.24 mol) at −78° C. The mixture was stirred at 0° C. for 2 hours. The iodo-compound of Example 7 (39 g, 0.124 mol) in THF (500 mL) was then added at 0° C., and the mixture was stirred at room temperature overnight. The mixture was poured into a mixture of $CH_2Cl_2$ (2 L) and cold 1 N HCl (1.5 L). After aqueous work-up ($CH_2Cl_2$) and chromatography, 17.7 g of the title compound was obtained: $[\alpha]^{25}_D$ -2.98° (c 0.57, $CHCl_3$). IR: 1719. $^1H$ NMR ($CDCl_3$): δ0.01 (3H, s), 0.01 (3H, s), 0.86 (9H, s), 0.86 (3H, d, J=5.7), 2.12 (3H, s), 2.15 (2H, m), 2.57 (1H, m), 3.33 (1H, dd, J=6.2, 9.8), 3.46 (1H, dd, J=4.6, 9.8). $^{13}C$ NMR ($CDCl_3$): δ –5.5, 16.7, 18.3, 25.9, 30.4, 32.2, 47.6, 67.5, 208.9.

EXAMPLE 9

Diene 21

To a solution of the compound of Example 6 (32 g, 0.090 mol) in anhydrous ether (400 mL) at −78° C. was added t-BuLi (116 mL of a 1.7 M solution in pentane, 0.197 mol). The mixture was stirred at −78° C. for 90 min. The compound of Example 8 (12.3 g, 53.5 mmol) in 100 mL of THF was added at −78° C. The mixture was stirred at −78° C. for 2 hours and was warmed up to room temperature. After aqueous work-up ($CH_2Cl_2$) and chromatography, 20.73 g of tertiary alcohol 20 was obtained, which was used directly in the next step.

To a solution of the tertiary alcohol (20 g, 43.5 mmol) in $CH_2Cl_2$ (400 mL) at room temperature was added Martin's sulfurane reagent until TLC analysis of the mixture indicated the completion of the reaction. The mixture was then concentrated in vacuo and chromatographed to give 18.26 g of the title compound and its diene isomers (95:5). A small amount was further purified by PTLC to give an analytical sample: $[\alpha]^{25}_D$ -35.1° (c 0.84, $CHCl_3$). IR: 1622. $^1H$ NMR ($CDCl_3$): δ0.00 (9H, s), 0.00 (3H, s), 0.01 (3H, s), 0.80 (3H, d, J=6.6), 0.86 (3H, t, J=7.3), 0.87 (9H, s), 0.88–0.94 (2H, m), 1.50–1.65 (2H, m), 1.64–1.70 (1H, m), 1.69 (3H, d, J=1.4), 1.77 (1H, dd, J=8.7, 13.3), 2.26 ($^1H$, dd, J=5.2, 13.3), 3.35 (1H, dd, J=6.2, 9.8), 3.39 ($^1H$, dd, J=5.7, 9.8), 3.49 (1H, m), 3.74 (1H, m), 3.84 (1H, t, J=7.0), 4.57 (2H, AB q, J=6.7), 4.86 (1H, s), 4.99 (1H, d, J=0.9), 5.74 (1H, s). $^{13}C$ NMR ($CDCl_3$): δ –5.4, –5.0, –1.4, 10.4, 12.7, 16.4, 18.1, 25.7, 25.9, 26.6, 34.5, 41.6, 65.1, 67.9, 83.3, 91.7, 115.1, 129.5, 136.5, 144.0.

EXAMPLE 10

Desilylated-21

To a solution of the compound of Example 9 (9.8 g, 0.022 mol) in DMF (250 mL) was added $Et_4NF$ (16.5 g, 0.111 mol). The mixture was stirred at room temperature overnight and was then concentrated in vacuo. After aqueous work-up (ether) and chromatography, 6.1 g of the title compound was obtained: $[\alpha]^{25}_D$ -78.4° (c 0.58, $CHCl_3$). IR: 3454, 1629. $^1H$ NMR ($CDCl_3$); δ0.00 (9H, s), 0.86 (3H, d, J=3.2), 0.87 (3H, t, J=3.7), 0.92 (2H, m), 1.50–1.66 (2H, m), 1.69 (3H, d, J=1.2), 1.71 (1H, m), 1.88 (1H, dd, J=8.2, 13.5), 2.23 (1H, dd, J=6.0, 13.5), 3.42 (1H, dd, J=5.9, 10.7), 3.46 (1H, dd, J=5.8, 10.7), 3.50 (1H, m), 3.73 (1H, m), 3.85 (1H, t, J=7.0), 4.57 (2H, AB q, J=6.8), 4.88 (1H, s), 5.03 (1H, d, J=0.9), 5.76 (1H, s). $^{13}C$ NMR ($CDCl_3$): δ –1.3, 10.7, 13.0, 16.7, 18.9, 27.6, 35.7, 42.8, 66.2, 68.2, 84.8, 92.8, 115.9, 130.8, 137.9, 145.3. HRMS (EI) calcd for $C_{18}H_{36}Si_1O_3$ 328.2344, found 328.2499.

EXAMPLE 11

Ethyl ester 24

To a solution of oxalyl chloride (5.6 mL, 0.064 mol) in $CH_2Cl_2$ (150 mL) at −78° C. was slowly added DMSO (6.1 mL, 0.086 mol). The mixture was stirred at −78° C. for 15 min. To this mixture was added the compound of Example 10 (3.5 g, 0.011 mol) in 50 mL of $CH_2Cl_2$. The mixture was stirred at −78° C. for 1 hour and $NEt_3$ (14.9 mL, 0.107 mol) was added. The mixture was stirred at −78° C. for another 15 min. After aqueous work-up ($CH_2Cl_2$) and chromatography, 3.24 g of the aldehyde was obtained, which was used directly in the next step.

To a mixture of LiCl (1.69 g, 0.040 mol) and phosphonate 31 (8.52 mL, 0.040 mol) in $CH_3CN$ (100 mL) was added DBU (4.46 mL, 0.030 mol). The mixture was stirred at room temperature until a clear solution was obtained, and was then cooled to 0° C. To this mixture was added the aldehyde obtained above (3.24 g, 9.94 mmol) in 30 mL of $CH_3CN$. The mixture was stirred at 0° C. for another hour and was concentrated in vacuo. After aqueous work-up ($CH_2Cl_2$) and chromatography, 3.87 g the title compound was obtained: $[\alpha]^{25}_D$ -21.60° (c 0.38, $CHCl_3$). IR: 1644, 1712. $^1H$ NMR ($CDCl_3$): δ0.00 (9H, s), 0.87 (3H, t, J=7.4), 0.92 (2H, m), 0.95 (3H, d, J=6.9), 1.27 (3H, t, J=7.1), 1.50–1.65 (2H, m), 1.66 (3H, s), 1.77 (3H, s), 2.06 (1H, dd, J=7.5, 13.5), 2.13 (1H, dd, J=6.9, 13.5), 2.58 (1H, m), 3.49 (1H, m), 3.74 (1H, m), 3.85 (1H, t, J=6.9), 4.16 (2H, AB q, J=7.2), 4.57 (2H, AB q, J=6.7), 4.86 (1H, s), 5.00 (1H, d, J=1.1), 5.73 (1H, s), 6.51 (1H, d, J=9.9). $^{13}C$ NMR ($CDCl_3$): δ –1.4, 10.4, 12.4, 12.8, 14.3, 18.1, 19.4, 26.6, 32.1, 44.7, 60.4, 65.1, 83.1, 91.7, 115.7, 126.4, 129.0, 137.2, 142.9, 147.2, 168.4. HRMS (EI) calcd for $C_{23}H_{42}Si_1O_4$ 410.2762, found 410.2752.

EXAMPLE 12

Alcohol 32

To a solution of the compound of Example 11 (3.60 g, 8.78 mmol) in $CH_2Cl_2$ (200 mL) at −78° C. was added DIBAL-H (44 mL of a 1 M solution in hexanes, 44 mmol). The mixture was stirred at −78° C. for 2 hours. EtOAc (20 mL) was added to quench the excess DIBAL-H. The mixture was warmed to room temperature. MeOH (10 mL) was added at 0° C., followed by saturated $NH_4Cl$ solution (300 mL) and cold 1N HCl (100 mL). After aqueous work-up and chromatography, 3.10 g of the title compound was obtained: $[\alpha]^{25}_D$ -48.5° (c 0.48, $CHCl_3$). IR: 3413, 1621. $^1H$ NMR ($CDCl_3$): δ0.00 (9H, s), 0.87 (3H, t, J=7.3), 0.89 (3H, d, J=6.4), 0.92 (2H, m), 1.50–1.65 (2H, m), 1.60 (3H, d, J=0.9), 1.66 (3H, d, J=1.2), 1.99–2.08 (2H, m), 2.48 (1H, m), 3.50 (1H, m), 3.74 (1H, m), 3.86 (1H, t, J=6.8), 3.94 (2H, s), 4.58 (2H, AB q, J=6.8), 4.84 (1H, s), 4.98 (1H, s), 5.18 (1H, d, J=9.4), 5.75 (1H, s). $^{13}C$ NMR ($CDCl_3$): δ –1.4, 10.4, 12.7, 13.7, 18.1, 20.5, 26.5, 31.4, 45.6, 65.1, 68.8, 83.2, 91.5, 115.2, 129.7, 132.0, 133.4, 136.4, 143.8.

EXAMPLE 13

Iodo-compound 25

To a mixture of the alcohol obtained above (1.05 g, 2.85 mol), $PPh_3$ (1.50 g, 5.72 mmol) and imidazole (389 mg, 5.72 mmol) in ether (30 mL) and $CH_3CN$ (10 mL) at −30° C. was added $I_{12}$ (1.45 g, 5.71 mmol). The mixture was stirred at −30° C. for 30 min and was then filtered through a plug of silica gel. The filtrate was concentrated in vacuo and the crude title compound obtained (1.50 g) was used in the next step directly without further purification.

EXAMPLE 14

(S)-Methyl 2,3-dihydroxypropionate

Acetonide 22 (58.5 g, 0.365 mol) was dissolved in MeOH (250 mL) and $H_2O$ (250 mL). To this mixture was added p-TsOH (34.7 g, 0.182 mol). The mixture was stirred at room temperature for 3 hours. NEt$_3$ (50 mL, 0.359 mol) was added. The mixture was concentrated in vacuo and chromatographed to give 35.53 g of the title compound: $[\alpha]^{25}_D$-8.3° (c 0.81, CHCl$_3$). IR: 3384, 1740. $^1$H NMR (D$_2$O): δ3.82 (3H, s), 3.88–3.89 (2H, m), 4.43 (1H, dd, J=3.8, 4.2). $^{13}$C NMR (D$_2$O): δ53.6, 64.2, 72.6, 175.3 (a small amount of CD$_3$OD was added as a reference).

EXAMPLE 15

Acetal 23

To a solution of the diol obtained above (35 g, 0.292 mol) in CHCl$_3$ (400 mL) were added 2,4,6-trimethylbenzaldehyde (86 mL, 0.583 mol), (±)-camphorsulfonic acid (6.78 g, 0.029 mol), powdered 4 Å molecular sieves (20 g) and MgSO$_4$ (10 g). The mixture was refluxed for 2 days with a Dean-Stark trap filled with 4Å pellet molecular sieves. NEt$_3$ (10 mL, 0.0717 mol) was added, and the mixture was filtered through celite. The filtrate was concentrated in vacuo and chromatographed to give 6.78 g of the cis-isomer of the title compound and 29.17 g of the title compound: $[\alpha]^{25}_D$-17.6° (c 0.58, MeOH). IR: 1747. $^1$H NMR (CD$_3$OD): δ2.17 (3H, s), 2.30 (6H, s), 3.74 (3H, s), 3.90 (1H, dd, J=6.6, 8.5), 4.45 (1H, dd, J=7.8, 8.5), 4.73 (1H, dd, J=6.6, 7.8), 6.18 (1H, s), 6.75 (2H, s). $^{13}$C NMR (CD$_3$OD): δ20.0, 21.0, 52.8, 69.0, 74.5, 104.5, 128.7, 130.9, 139.5, 140.2, 173.6.

EXAMPLE 16

Methyl ester 26

To a mixture of the crude compound obtained in Example 14 (1.50 g) and the compound obtained in Example 15 (5.71 g, 22.8 mmol) in THF (150 mL) and HMPA (50 mL) at -78° C. was added LiHMDS (25.7 mL of a 1 M solution in THF, 25.7 mmol). The mixture was stirred at -78° C. for 1 hour. After aqueous work-up and chromatography, 1.28 g of the title compound was obtained: $[\alpha]^{25}_D$-28.2° (c 0.65, EtOAc). IR: 1749, 1614. $^1$H NMR (C$_6$D$_6$): δ-0.01 (9H, s), 0.93 (3H, t, J=7.3), 0.93 (3H, d, J=7.1), 0.94 (2H, m), 1.57 (1H, m), 1.75 (1H, m), 1.77 (3H, s), 1.77 (3H, s), 1.93 (1H, dd, J=8.2, 13.2), 2.07 (3H, s), 2.15 (1H, dd, J=5.7, 13.2), 2.47 (6H, s), 2.54 (1H, d, J=13.8), 2.58 (1H, m), 2.65 (1H, d, J=13.8), 3.40 (3H, s), 3.52 (1H, m), 3.83 (1H, m), 3.83 (1H, d, J=8.3), 3.99 (1H, t, J=6.7), 4.3 (1H, d, J=8.3), 4.59 (1H, d, J=6.8), 4.74 (1H, d, J=6.8), 4.95 (1H, s), 5.04 (1H, s), 5.12 (1H, d, J=9.1), 5.86 (1H, s), 6.46 (1H, s), 6.69 (2H, s). $^{13}$C NMR (C$_6$D$_6$): δ-1.3, 10.6, 13.0, 17.4, 18.3, 20.2, 20.3, 20.9, 27.1, 31.4, 46.0, 46.2, 51.5, 65.2, 73.2, 83.3, 85.3, 92.1, 103.6, 115.4, 128.3, 128.6, 129.6, 130.4, 136.1, 137.5, 138.5, 138.7, 144.1, 173.0. HRMS (EI) calcd for C$_{35}$H$_{56}$Si$_1$O$_6$ 600.3756, found 600.3800.

EXAMPLE 17

Deprotected 26

To a solution of the compound of Example 16 (467 mg, 0.778 mmol) in DMSO (20 mL) was added Et$_4$NF (1.16 g, 7.77 mmol) and 2 g of powdered 4 Å molecular sieves. The mixture was stirred at 90° C. overnight, and was then acidified with 1N HCl. After aqueous work-up (ether) and concentration in vacuo, the mixture was dissolved in ether (20 mL) to which ethereal CH$_2$N$_2$ was added until a steady yellow color was obtained. The mixture was stirred for another 5 min and nitrogen was passed through the mixture to remove the excess CH$_2$N$_2$. The mixture was concentrated in vacuo and chromatographed to give 190.2 mg of the deprotected compound: $[\alpha]^{25}_D$+7.6° (c 0.29, EtOAc). IR: 3477, 1741, 1610. $^1$H NMR (C$_6$D$_6$): δ0.84 (3H, t, J=7.5), 0.93 (3H, d, J=6.6), 1.47 (2H, m), 1.71 (3H, s), 1.72 (3H, s), 1.98 (1H, dd, J=7.3, 13.5), 2.07 (3H, s), 2.12 (1H, dd, J=6.6, 13.5), 2.47 (6H, s), 2.52 (1H, d, J=13.9), 2.53 (1H, m), 2.64 (1H, d, J=13.9), 3.38 (3H, s), 3.74 (1H, t, J=6.4), 3.82 (1H, d, J=8.1), 4.28 (1H, J=8.1), 4.93 (1H, s), 5.03 (1H, s), 5.11 (1H, d, J=9.4), 5.80 (1H, s), 6.46 (1H, s), 6.70 (2H, s). $^{13}$C NMR (C$_6$D$_6$): δ10.2, 13.6, 17.4, 20.3, 20.6, 20.9, 28.3, 31.6, 46.1, 46.2, 51.6, 73.3, 78.8, 85.3, 103.7, 115.1, 126.3, 128.3, 128.6, 129.6, 130.4, 136.0, 138.5, 138.8, 140.8, 144.4, 173.1. HRMS (EI) calcd for C$_{29}$H$_{42}$O$_5$ 470.3032, found 470.3080.

EXAMPLE 18

Acetate 27

The compound of Example 17 (165.2 mg, 0.351 mmol) was dissolved in 10 mL of pyridine and 5 mL of acetic anhydride. DMAP (10 mg, 0.082 mmol) was added and the mixture was stirred at room temperature for 1 hour. The mixture was concentrated in vacuo and chromatographed to give 178.2 mg of the title compound: $[\alpha]^{25}_D$+1.40° (c 0.18, EtOAc). IR: 1733, 1610. $^1$H NMR (C$_6$D$_6$): δ0.76 (3H, t, J=7.5), 0.90 (3H, d, J=6.7), 1.46–1.63 (2H, m), 1.67 (3H, s), 1.75 (3H, s), 1.76 (3H, s), 1.92 (1H, dd, J=8.0, 13.5), 2.07 (3H, s), 2.10 (1H, dd, J=6.4, 13.5), 2.46 (6H, s), 2.54 (1H, d, J=14.0), 2.55 (1H, m), 2.64 (1H, d, J=14.0), 3.39 (3H, s), 3.83 (1H, d, J=8.3), 4.30 (1H, d, J=8.3), 4.91 (1H, s), 5.01 (1H, s), 5.10 (1H, d, J=9.4), 5.22 (1H, t, J=6.9), 5.92 (1H, s), 6.46 (1H, s), 6.69 (2H, s). $^{13}$C NMR (C$_6$D$_6$): δ9.96, 13.8, 17.3, 20.3, 20.7, 20.9, 26.0, 31.4, 45.9, 46.2, 51.5, 73.2, 80.4, 85.3, 103.6, 115.5, 128.3, 128.6, 129.1, 129.7, 130.4, 136.0, 136.0, 138.5, 138.7, 143.9, 169.3, 173.0. HRMS (EI) calcd for C$_{31}$H$_{44}$O$_6$ 512.3138, found 512.3126.

EXAMPLE 19

Cyclization product 28

To a solution of the compound of Example 18 (91.2 mg, 0.178 mmol) in THF (100 mL) at 0° C. was added LiHMDS (1.07 mL of a 1 M THF solution, 1.07 mmol). This mixture was added over 1 hour to a 2-necked flask containing 100 mL of THF under reflux. After the addition was complete, the mixture was stirred under reflux for another hour. The mixture was concentrated in vacuo. After aqueous work-up and purification by PTLC, 64.1 mg of the title compound was obtained: $[\alpha]^{25}_D$-7.5° (c 0.067, EtOAc). IR: 1742, 1712, 1607. $^1$H NMR (C$_6$D$_6$): δ0.85 (3H, t, J=7.5), 0.91 (3H, d, J=6.7), 1.46 (1H, m), 1.47 (3H, s), 1.58 (3H, s), 1.62 (1H, m), 1.98 (1H, dd, J=8.5, 13.1), 2.07 (3H, s), 2.27 (1H, dd, J=2.5, 13.1), 2.32(6H, s), 2.56(11H, m), 2.6(2H, AB q, J=14.4), 3.23 (1H, d, J=16.2), 3.91 (1H, d, J=8.3), 3.95 (1H, d, J=16.2), 4.15 (1H, d, J=8.3), 4.87 (1H, s), 5.01 (1H, d, J=2.0), 5.19 (1H, d, J=9.2), 5.38 (1H, dd, J=4.2, 7.4), 5.89 (1H, s), 6.02 (1H, d, J=1.3), 6.69 (2H, s). $^{13}$C NMR (C$_6$D$_6$): δ9.5, 15.8, 16.3, 20.3, 20.9, 21.1, 26.4, 33.8, 45.6, 45.6, 47.2, 72.1, 77.9, 88.9, 102.0, 115.3, 126.4, 127.6, 128.3, 130.4, 134.2, 137.1, 138.3, 139.0, 144.2, 165.4, 204.0. HRMS (EI) calcd for C$_{30}$H$_{40}$O$_5$ 480.2876, found 480.2900.

EXAMPLE 20

Compound 29

To a solution of the compound of Example 19 (32.0 mg, 0.0667 mmol) in anhydrous DMF (2.5 mL) at 0° C. was added KOt-Bu (0.077 mL of a 1 M THF solution, 0.077 mmol). The mixture was stirred at 0° C. for 10 min. MeI (0.021 mL, 0.337 mmol) was added at 0° C. and stirring was continued for 1 hour. The mixture was concentrated in vacuo and was purifed by PTLC to give 30.3 mg (92% yield) of the title compound: $[\alpha]^{25}_D$+20.2° (c 0.19, EtOAc). IR: 1749, 1712, 1607. $^1$H NMR ($C_6D_6$): δ0.76 (3H, t, J=7.3), 0.85 (3H, d, J=6.9), 1.46 (3H, d, J=6.9), 1.51 (3H, s), 1.52 (2H, m), 1.56 (3H, s), 1.84 (1H, dd, J=10.6, 12.8), 2.07 (3H, s), 2.08 (1H, dd, J=2.7, 12.8), 2.39 (6H, s), 2.40 (1H, m), 2.71 (1H, d, J=16.5), 3.0 (1H, d, J=16.5), 4.05 (1H, d, J=8.7), 4.26 (1H, q, J=6.9), 4.75 (1H, s), 4.78 (1H, d, J=8.4), 4.98 (1H, d, J=2.0), 5.00 (1H, d, J=9.6), 5.27 (1H, t, J=6.3), 5.96 (1H, s), 6.07 (1H, s), 6.70 (2H, s). $^{13}$C NMR ($C_6D_6$): δ9.5, 15.3, 16.1, 18.9, 20.4, 20.9, 22.4, 26.1, 35.8, 43.7, 45.6, 47.0, 69.7, 79.8, 88.2, 102.6, 114.5, 127.7, 128.3, 129.0, 130.5, 134.2, 134.2, 138.3, 139.1, 145.9, 169.1, 206.7. HRMS (EI) calcd for $C_{31}H_{42}O_5$ 494.3032, found 494.3007.

EXAMPLE 21

Compound 30

To a solution of the compound of Example 20 (9.8 mg, 0.020 mmol) in DMF (1 mL) at 0° C. was added KOt-Bu (0.030 mL of a 1 M THF solution, 0.030 mmol). The mixture was stirred at 0° C. for 10 min. Glacial AcOH (0.010 mL, 0.175 mmol) was added, and the mixture was concentrated in vacuo and purifed by PTLC to give 9.1 mg of the title compound: $[\alpha]^{25}_D$-99.4° (c 0.14, EtOAc). IR: 1742, 1712, 1607. $^1$H NMR ($C_6D_6$): δ0.86 (3H, d, J=7.0), 0.87 (3H, t, J=7.6), 1.30 (3H, d, J=6.8), 1.55 (2H, m), 1.72 (3H, s), 1.82 (3H, s), 2.03 (1H, dd, J=7.8, 13.3), 2.06 (3H, s), 2.29 (1H, br d, J=13.3), 2.38 (1H, d, J=14.2), 2.45 (6H, s), 2.46 (1H, m), 3.06 (1H, d, J=14.2), 3.53 (1H, q, J=6.9), 3.62 (1H, d, J=8.7), 3.90 (1H, d, J=8.7), 4.80 (1H, s), 4.92 (1H, t, J=6.1), 4.97 ($^1$H, s), 5.32 (1H, d, J=9.4), 5.99 (1H, s), 6.16 (11H, s), 6.68 (2H, s). $^{13}$C NMR ($C_6D_6$): δ10.0, 16.1, 16.2, 18.5, 19.7, 20.3, 20.9, 26.6, 32.7, 43.7, 45.6, 50.5, 72.0, 80.7, 91.1, 103.1, 116.3, 127.0, 128.5, 129.5, 130.4, 134.7, 136.3, 138.4, 138.8, 144.7, 167.6, 202.5. HRMS (EI) calcd for $C_{31}H_{42}O_5$ 494.3032, found 494.3018.

EXAMPLE 22

Synthetic C2-epi-Galbonolide B

The compound of Example 20 (6.6 mg, 0.0134 mmol) was dissolved in 2 mL of glacial AcOH and 1 mL of $H_2O$. The mixture was stirred at room temperature for 30 min. It was then concentrated in vacuo and purified by PTLC to give 4.7 mg of C2-epi-galbonolide B: $[\alpha]^{25}_D$-2.10° (c 0.20, EtOAc). IR: 3484, 1735, 1712, 1614. $^1$H NMR ($CD_3OD$): δ 0.84 (3H, t, J=7.4), 0.87 (3H, d, J=6.9), 1.16 (3H, d, J=7.1), 1.56 (3H, s), 1.66 (2H, m), 1.75 (3H, s), 1.92 (1H, dd, J=10.6, 12.8), 2.14 (1H, d, J=14.0), 2.26 (1H, dd, J=3.2, 12.8), 2.38 (1H, d, J=14.0), 2.44 (1H, m), 3.52 (1H, d, J=10.8), 3.63 (1H, d, J=10.8), 3.85 (1H, q, J=7.1), 4.87 (1H, s), 4.93 (1H, t, J=6.9), 5.05 (1H, s), 5.14 (1H, d, J=9.0), 5.87 (1H, s). $^{13}$C NMR ($CD_3OD$): δ10.1, 13.1, 14.6, 18.0, 22.0, 26.5, 36.4, 45.8, 46.9, 51.4, 70.0, 81.5, 83.1, 116.8, 130.3, 132.5, 136.1, 139.8, 145.9, 169.6, 173.6, 213.1. HRMS (EI) calcd for $C_{21}H_{32}O_5$ 364.2250, found 364.2288.

EXAMPLE 23

Synthetic Galbonolide B

The compound of Example 21 (6.7 mg, 0.0136 mmol) was dissolved in 2 mL of glacial AcOH and 1 mL of $H_2O$. The mixture was stirred at room temperature for 30 min. It was then concentrated in vacuo and purified by PTLC to give 4.7 mg of synthetic galbonolide B: $[\alpha]^{25}_D$-95.3° (c 0.22, EtOAc). IR: 3469, 1734, 1712, 1614. $^1$H NMR ($CD_3OD$): δ0.70 (3H, d, J=6.8), 0.90 (3H, t, J=7.4), 1.39 (3H, d, J=6.9), 1.60–1.74 (2H, m), 1.61 (3H, d, J=1.3), 1.75 (3H, d, J=1.3), 1.99 (1H, d, J=13.9), 2.08 (1H, dd, J=7.6, 13.0), 2.18 (1H, br d, J=13.0), 2.46 (1H, m), 2.65 (1H, d, J=13.9), 3.54 (1H, d, J=11.7), 3.88 (1H, d, J=11.7), 3.94 (1H, q, J=7.0), 4.74 (1H, s), 4.81 (1H, dd, J=4.3, 7.9), 4.94 (1H, d, J=8.5), 4.97 (1H, s), 5.62 (1H, s). $^{13}$C NMR ($CD_3OD$): δ10.3, 15.7, 16.3, 19.1, 19.6, 27.4, 33.9, 42.6, 46.5, 51.1, 69.0, 82.0, 85.6, 117.1, 128.2, 129.6, 136.1, 137.6, 145.3, 170.4, 209.9. HRMS (EI) calcd for $C_{21}H_{32}O_5$ 364.2250, found 364.2257.

The following examples illustrate the preparation of some of the novel analogs of Galbonolide B and are not to be construed as limiting the invention disclosed herein.

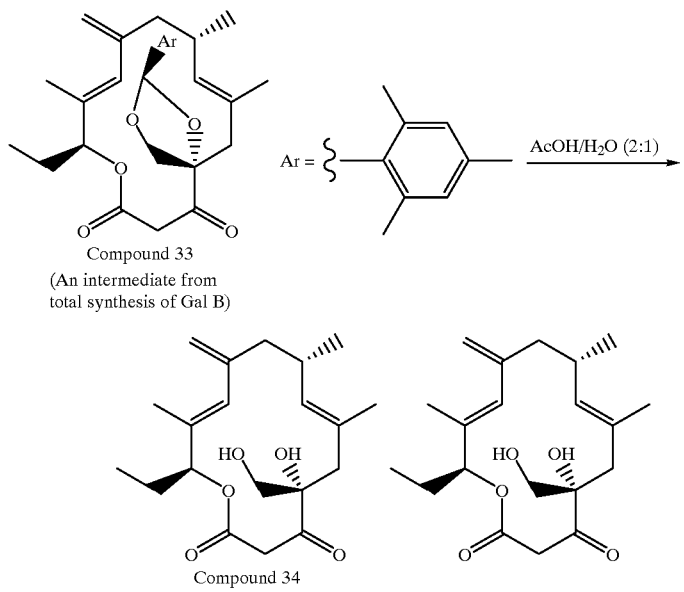

Compound 33
(An intermediate from total synthesis of Gal B)

Compound 34

EXAMPLE 24

To 2.9 mg of Compound 33 was added glacial AcOH (2 mL) and H$_2$O (1 mL). The mixture was stirred at room temperature for 30 minutes. After concentration in vacuo and purification by PTLC, 1.9 mg of the above compound was obtained. $^1$H NMR (CDCl$_3$): δ0.91 (3H, t, J=7.4), 0.92 (3H, d, J=6.9), 1.62 (3H, s), 1.72 (2H, m), 1.82 (3H, s), 2.04 (1H, dd, J=10.6, 12.8), 2.28 (1H, d, J=10.8), 2.30 (1H, dd, J=3.2, 12.8), 2.50 (1H, m), 2.60 (1H, d, J=10.8), 3.40 (1H, d, J=10.8), 3.60 (1H, d, J=10.8), 3.65 (1H, d, J=10.0), 3.79 (1H, d, J=10.0), 4.97 (1H, s), 5.00 (1H, t, J=6.9), 5.12 (1H, s), 5.29 (1H, d, J=8.5), 5.91 (1H, s). MS (CI): m/z=368 (M+NH$_4$).

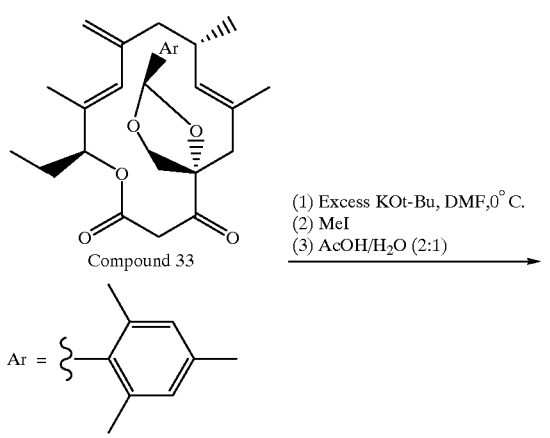

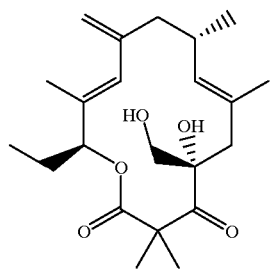

EXAMPLE 25

To a solution of Compound 33 (5.3 mg) in DMF (1 mL) was added excess KOt-Bu (50 µL of a 1 M THF solution) at 0° C. The mixture was stirred at 0° C. for 5 minutes. Excess MeI (30 µL) was added. The mixture was stirred at 0° C. for 1 hour. After concentration in vacuo and purification by PTLC, the dimethylated product was treated with AcOH (2 mL) and H$_2$O (1 mL). The mixture was stirred at room temperature for 30 minutes. After concentration in vacuo and purification by PTLC, the above compound was obtained. MS (CI): m/z=396 (M+NH$_4$).

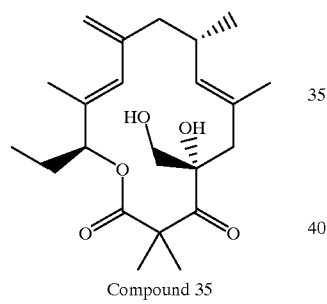

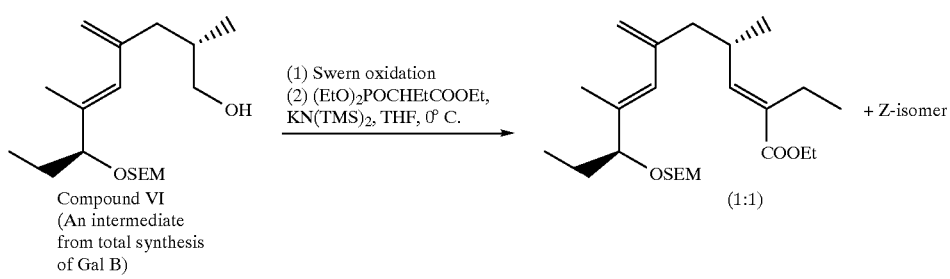

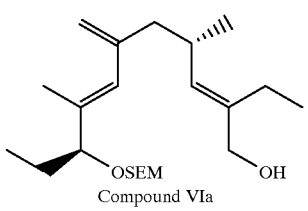

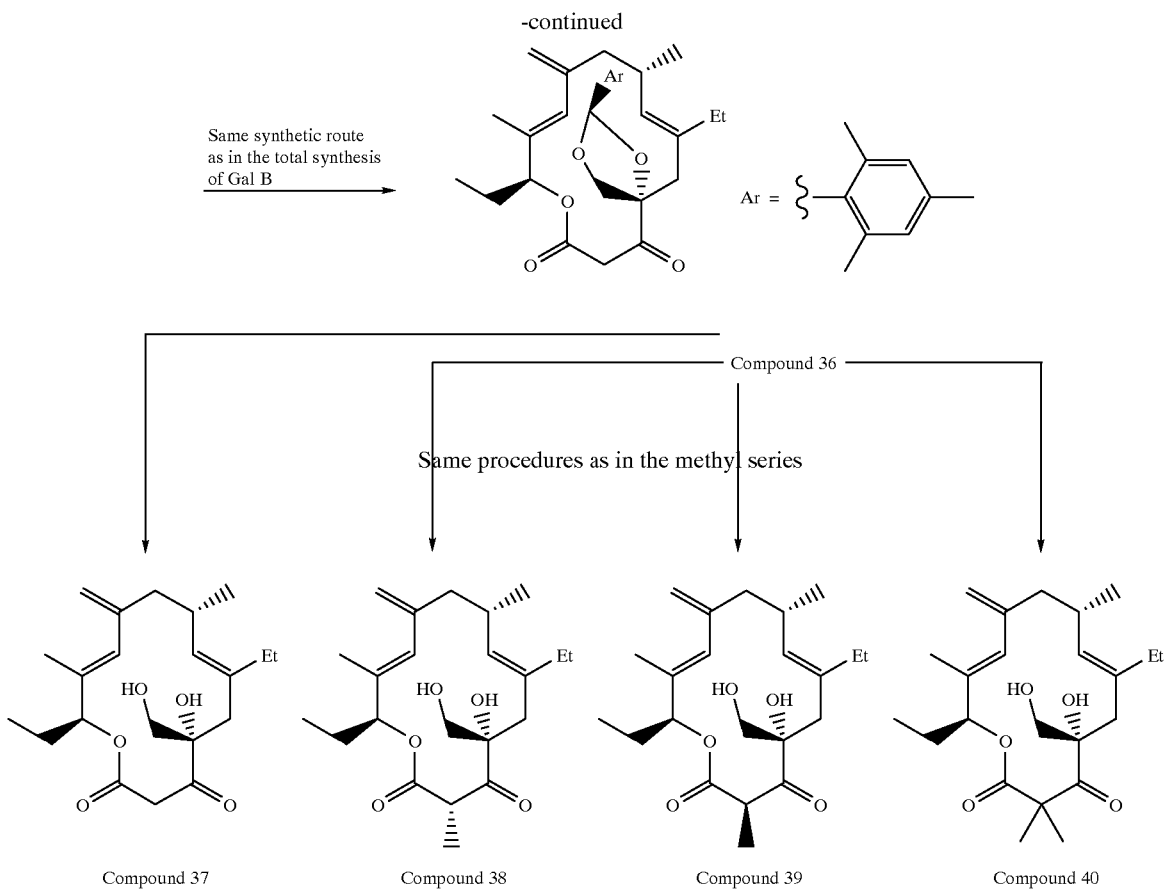

The preparation of the C6-ethyl series of compounds diverted from the C6-methyl series at the stage of Compound VI. The same Swern oxidation conditions as in the methyl series was first carried out to yield the corresponding aldehyde.

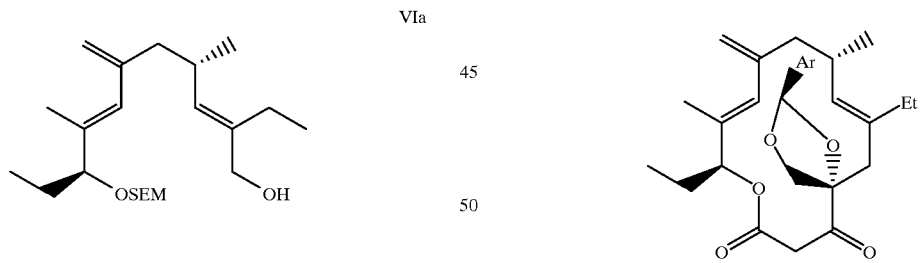

EXAMPLE 27

To a solution of $(EtO)_2POCHEtCOOEt$ (9.8 mL) in 100 mL of THF was added $KN(TMS)_2$ (66 mL of a 0.5 m solution in toluene) at 0° C. The mixture was stirred at 0° C. for 10 minutes. The aldehyde obtained above (1.88 g) in THF was added at 0° C. The mixture was stirred at 0° C. for 2 hours. After aqueous work-up $(CH_2Cl_2)$ and chromatography, 1.48 g of the desired E- and the undesired Z-ethyl ester (1:1) was obtained, which was dissolved in 40 mL of $CH_2Cl_2$. DIBAL-H (21 mL of a 1 M solution in hexanes) was added at −78° C. The mixture was stirred at −78° C. for 2 hours. The excess DIBAL-H was quenched with EtOAc. Dilute HCl was added. After aqueous work-up and chromatography, 0.74 g of the above intermediate compound was obtained. $^1H$ NMR $(CDCl_3)$: δ0.00 (9H, s), 0.88 (3H, t, J=6.7), 0.90 (3H, d, J=6.9), 0.90 (2H, m), 0.97 (3H, t, J=6.8), 1.55 (2H, m), 1.67 (3H, s), 2.00–2.10 (4H, m), 2.50 (1H, m), 3.50 (1H, m), 3.74 (1H, m), 3.87 (1H, t, J=6.7), 3.98 (2H, s), 4.60 (2H, m), 4.84 (1H, s), 4.98 (1H, s), 5.15 (1H, d, J=6.0), 5.74 (1H, s).

EXAMPLE 28

To prepare the above compound from the compound of Example 27, the same procedure to obtain Compound 33 as in the total synthesis was followed. $^1H$ NMR $(CDCl_3)$: δ0.86 (3H, t, J=7.1), 0.91 (3H, d, J=6.9), 0.97 (3H, t, J=7.2), 1.70 (2H, m), 1.72 (3H, s), 1.95 (1H, dd, J=10.6, 12.8), 2.25 (3H, s), 2.18–2.30 (3H, m), 2.40 (6H, s), 2.58 (1H, m), 2.64 (1H, d, J=10.8), 2.92 (1H, d, J=10.8), 3.34 (1H, d, J=11.0), 4.09 (1H, d, J=6.0), 4.10 (1H, d, J=11.0), 4.30 (1H, d, J=6.0), 4.80 (1H, s), 4.97 (1H, s), 5.14 (1H, d, J=6.7), 5.21 (1H, dd, J=6.0, 8.0), 5.72 (1H, s), 5.95 (1H, s), 6.82 (2H, s).

To prepare Compounds 37–40 from Compound 34, the same procedures to prepare Compound 34, C2-epigalbonolide B, galbonolide B and Compound 35 from Compound 33 were followed.

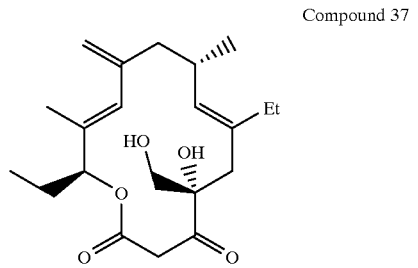

Compound 37

EXAMPLE 29A $^1$H NMR (CDCl$_3$): δ0.89 (3H, t, J=7.1), 0.90 (3H, d, J=6.9), 0.92 (3H, t, J=7.2), 1.70 (2H, m), 1.80 (3H, s), 2.04–2.30 (4H, m), 2.42 (2H, m), 2.52 (1H, m), 3.39 (1H, d, J=10.8), 3.60 (1H, d, J=10.8), 3.60 (1H, d, J=10.0), 3.78 (1H, d, J=10.0), 4.95 (1H, s), 4.97 (1H, t, J=6.9), 5.09 (1H, s), 5.21 (1H, d, J=8.5), 5.90 (1H, s).

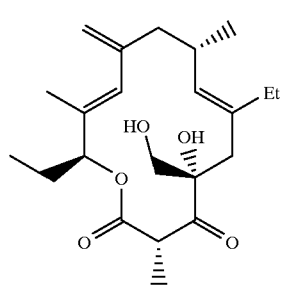

Compound 38

EXAMPLE 29B $^1$H NMR (CDCl$_3$): δ0.88 (3H, t, J=7.4), 0.92 (3H, t, J=7.2), 0.98 (3H, d, J=6.9), 1.24 (3H, d, J=7.1), 1.70 (2H, m), 1.82 (1H, d, J=14.0), 1.88 (3H, s), 2.00–2.60 (4H, m), 2.71 (1H, m), 2.86 (1H, d, J=14.0), 3.36 (1H, d, J=10.8), 3.53 (1H, d, J=10.8), 3.70 (1H, q, J=7.1), 4.95 (1H, d, J=9.0), 4.96 (1H, t, J=6.9), 5.02 (1H,s) 5.17 (1H, s), 5.95 (1H, s).

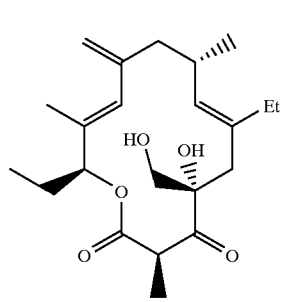

Compound 39

EXAMPLE 29C $^1$H NMR (CDCl$_3$): δ0.85–0.92 (9H, m),1.41 (3H, d, J=6.9),1.70 (2H, m), 1.79 (3H, s), 1.90–2.30 (4H, m), 2.11 (1H, d, J=13.0), 2.52 (1H, m), 2.72 (1H, d, J=13.0), 3.55 (1H, d, J=11.7), 3.78 (1H, q, J=7.0), 3.80 (1H, d, J=11.7), 4.85 (1H, s), 4.89 (1H, d, J=8.5), 5.04 (1H, s),5.05 (1H, m), 5.78 (1H, s).

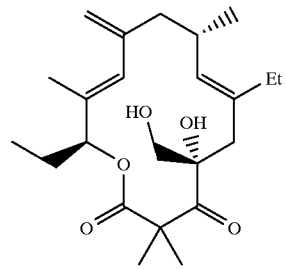

Compound 40

EXAMPLE 29D $^1$H NMR (CDCl$_3$): δ0.88 (3H, t, J=7.4), 0.94 (3H, t, J=7.4), 0.98 (3H, d, J=6.9), 1.24 (3H, s), 1.38 (3H, s), 1.70 (2H, m), 1.82 (3H, s), 2.00–2.60 (4H, m), 2.17 (1H, d, J=12.0), 2.75 (1H, d, J=12.0), 2.82 (1H, m), 2.82 (1H, d, J=12.0), 3.32 (1H, d, J=9.0), 3.53 (1H, d, J=9.0), 4.96 (1H, t, J=6.7), 5.00 (1H, d, J=6.7), 5.02 (1H, s), 5.17 (1H, s), 5.99 (1H, s).

In the total synthesis of Gal B:

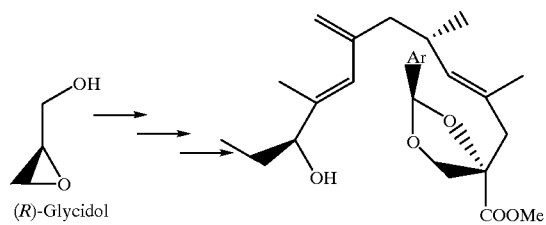

(R)-Glycidol

In the preparation of Compounds 41 and 42:

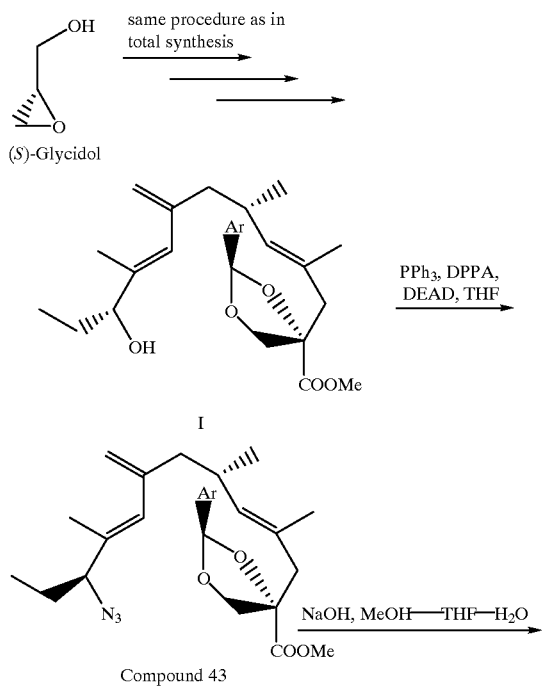

(S)-Glycidol

Compound 43

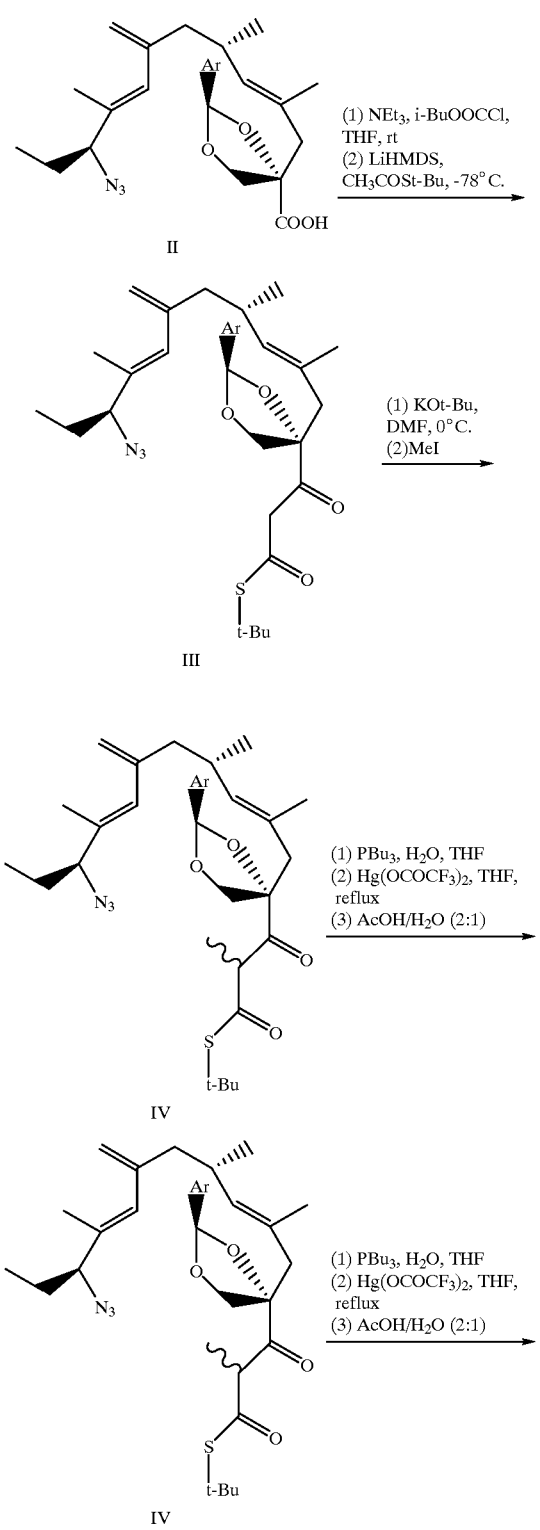
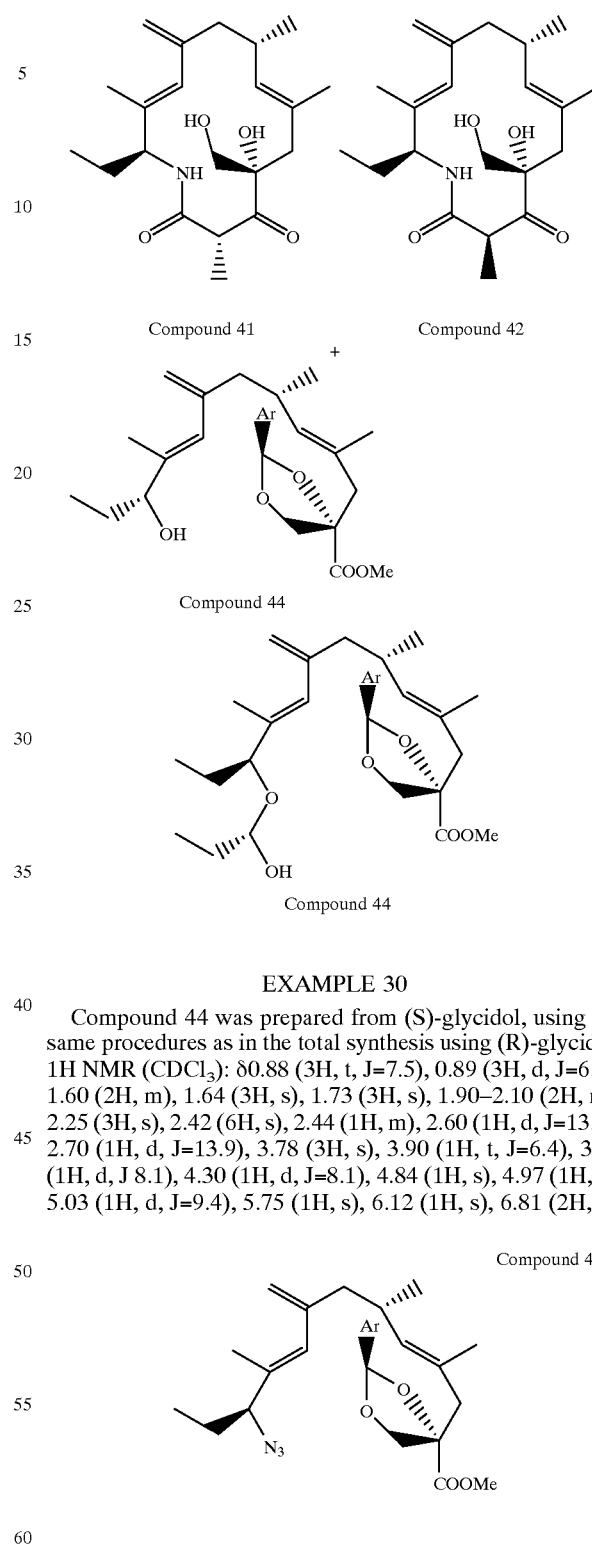
EXAMPLE 30
Compound 44 was prepared from (S)-glycidol, using the same procedures as in the total synthesis using (R)-glycidol. 1H NMR (CDCl$_3$): δ 0.88 (3H, t, J=7.5), 0.89 (3H, d, J=6.6), 1.60 (2H, m), 1.64 (3H, s), 1.73 (3H, s), 1.90–2.10 (2H, m), 2.25 (3H, s), 2.42 (6H, s), 2.44 (1H, m), 2.60 (1H, d, J=13.9), 2.70 (1H, d, J=13.9), 3.78 (3H, s), 3.90 (1H, t, J=6.4), 3.97 (1H, d, J 8.1), 4.30 (1H, d, J=8.1), 4.84 (1H, s), 4.97 (1H, s), 5.03 (1H, d, J=9.4), 5.75 (1H, s), 6.12 (1H, s), 6.81 (2H, s).

EXAMPLE 31

To a solution of Compound 44 (220 mg) in THF (7 mL) was added PPh$_3$ (368 mg). DEAD (0.22 mL) was then slowly added at 0° C., followed by DPPA (0.30 mL). The mixture was stirred at room temperature overnight. After purification by PTLC, 101.0 mg of Compound 43 was obtained. $^1$H NMR (CDCl$_3$): δ0.86 (3H, t, J=7.5), 0.87 (3H, d, J=6.6), 1.55 (2H, m), 1.63 (3H, s), 1.72 (3H, s), 1.85–2.08 (2H, m), 2.23 (3H, s), 2.39 (6H, s), 2.44 (1H, m), 2.58 (1H, d, J=13.9), 2.68 (1H, d, J=13.9), 3.72 (1H, t, J=6.4), 3.74 (3H, s), 3.95 (1H, d J=8.1), 4.29 (1H, d, J=8.1), 4.86 (1H, s), 4.99 (1H, s), 5.00 (1H, d, J=9.4), 5.73 (1H, s), 6.10 (1H, s), 6.79 (2H, s).

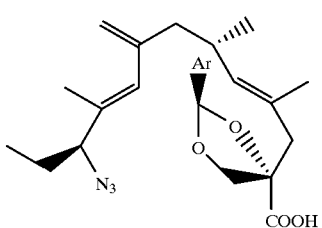

Compound 43a

EXAMPLE 32

Compound 43 (101 mg) was dissolved in THF (3 mL), MeOH (2 mL) and H$_2$O (3 mL). NaOH (2 mL of a 1 N solution) was added. The mixture was stirred at room temperature overnight. After acidification and aqueous work-up, 98 mg of the carboxylic acid, Compound 43a was obtained, which was used in the next step without further purification. $^1$H NMR (CDCl$_3$): δ0.87 (3H, t, J=7.5), 0.88 (3H, d, J=6.6), 1.54 (2H, m), 1.65 (3H, s), 1.70 (3H, s), 1.90–2.10 (2H, m), 2.24 (3H, s), 2.40 (6H, s), 2.55 (1H, m), 2.58 (1H, d, J=13.9), 2.70 (1H, d, J=13.9), 3.71 (1H, t, J=6.4), 4.02 (1H, d, J=8.1), 4.30 (1H, d, J=8.1), 4.85 (1H, s), 5.00 (1H, s), 5.09 (1H, d, J=9.4), 5.74 (1H, s), 6.10 (1H, s), 6.81 (2H, s).

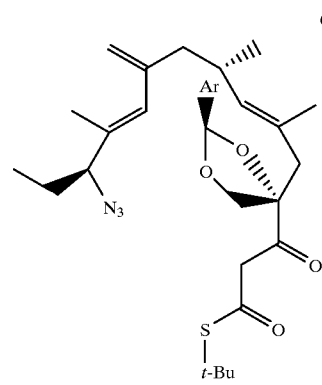

Compound 43b

EXAMPLE 33

LiHMDS (1.8 mL of a 1 M THF solution) was added to 5 mL of THF. tert-Butyl thioacetate (0.29 mL) was slowly added at −78° C. The mixture was stirred at −78° C. for 15 minutes. To a solution of the carboxylic acid, Compound 43a, (98 mg) in THF (5 mL) was added NEt$_3$ (58 μL), followed by iso-butyl chloroformate (40 μL). The mixture was stirred at room temperature for 30 minutes. The lithium enolate prepared above was added at −78° C. The mixture was stirred at −78° C. for 1 hour. After aqueous work-up and purification by PTLC, 56 mg of Compound 43b was obtained. $^1$H NMR (CDCl$_3$): δ0.80–0.90 (6H, m), 1.38 (9H, s), 1.50 (3H, s), 1.55 (2H, m), 1.70 (3H, s), 1.90–2.05 (2H, m), 2.24 (3H, s), 2.40 (6H, s), 2.45 (1H, m), 2.55 (1H, d, J=13.9), 2.62 (1H, d, J=13.9), 3.70–4.40 (5H, m), 4.80–5.80 (4H, m), 6.03 (1H, s), 6.81 (2H, s).

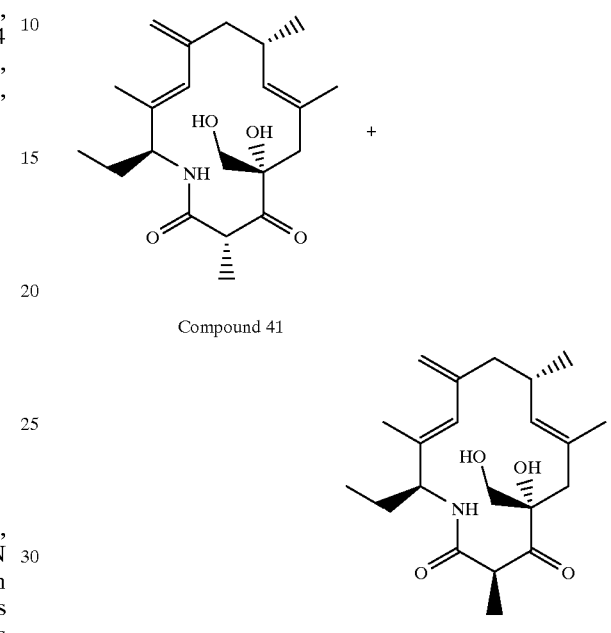

Compound 41

Compound 42

EXAMPLE 34

To a solution of Compound 43b (56 mg) in 3 mL of DMF was added KOt-Bu (0.1 mL of a 1 M solution in THF) at 0° C. The mixture was stirred at 0° C. for 10 minutes. MeI (29 μL) was added. The mixture was stirred at 0° C. for 2 hours. After concentration in vacuo and purification by PTLC, 30 mg of the methylated product was obtained, which was used directly in the next step.

To a solution of the methylated product (30 mg) in 5 mL of THF was added PBu$_3$ (50 μL) and 3 drops of water. The mixture was stirred at room temperature overnight, and was then concentrated and dried in vacuo. Fresh THF (5 mL) was added to the mixture, followed by Hg(OCOCF$_3$)$_2$ (42 mg). The mixture was refluxed for 4 hours. After concentration in vacuo and purification by PTLC, the crude cyclized products was dissolved in AcOH (4 mL) and H$_2$O (2 mL). The mixture was stirred at room temperature for 30 minutes. After concentration in vacuo and purification by PTLC, 0.3 mg of Compound 42 and 0.6 mg of Compound 41 were obtained.

Compound 41 $^1$H NMR (CD$_3$OD): δ0.83 (3H, d, J=6.8), 0.86 (3H, t, J=7.2), 1.28 (3H, d, J=7.0), 1.55 (2H, m), 1.59 (3H, s), 1.70 (3H, s), 1.88–2.10 (2H, m), 2.24 (1H, d, J=13.0), 2.40 (1H, d, J=13.0), 2.44 (1H, m), 3.14 (1H, q, J=7.0), 3.59 (2H, m), 3.88 (1H, t, J=6.7), 4.78 (1H, s), 4.99 (1H, s), 5.00 (1H, d, J=8.0), 5.76 (1H, s).

Compound 42 $^1$H NMR (CD$_3$OD): δ0.84 (3H, d, J=6.8), 0.86 (3H, t, J=7.2), 1.55 (2H, m), 1.60 (3H, s), 1.71 (3H, s), 1.74 (3H, d, J=7.0), 1.90–2.08 (2H, m), 2.24 (1H, d, J=13.0), 2.40 (1H, d, J=13.0), 2.43 (1H, m), 3.60 (2H, m), 3.88 (1H, t, J=6.7), 4.30 (1H, q, J=7.0), 4.78 (1H, s), 4.98 (1H, s), 5.00 (1H, d, J=8.0), 5.74 (1H, s).

The following examples illustrate representative compositions containing compounds of the invention.

EXAMPLE 35

1000 compressed tablets each containing 500 mg of the compound of formula (2) are prepared from the following formulation:

| Ingredient | Grams |
| --- | --- |
| Compound | 500 |
| Starch | 750 |
| Dibasic calcium phosphate, hydrous | 5000 |
| Calcium stearate | 2.5 |

The finely powdered ingredients are mixed well and granulated with 10 percent starch paste. The granulation is dried and compressed into tablets.

EXAMPLE 36

1000 hard gelatin capsules, each containing 500 mg of the same compound are prepared from the following formulation:

| Ingredient | Grams |
| --- | --- |
| Compound | 500 |
| Starch | 250 |
| Lactose | 750 |
| Talc | 250 |
| Calcium stearate | 10 |

A uniform mixture of the ingredients is prepared by blending and used to fill two-piece hard gelatin capsules.

EXAMPLE 37

An aerosol composition may be prepared having the following formulation:

| Ingredient | Per Canister |
| --- | --- |
| Compound | 24 mg |
| Lecithin NF Liquid Concd. | 1.2 mg |
| Trichlorofluoromethane, NF | 4.026 g |
| Dichlorodifluoromethane, NF | 12.15 g |

EXAMPLE 38

250 milliliters of an injectable solution may be prepared by conventional procedures having the following formulation:

| Dextrose | 12.5 g |
| --- | --- |
| Water | 250 ml |
| Compound | 400 mg |

The ingredients are blended and thereafter sterilized for use.

What is claimed is:

1. A compound of the formula

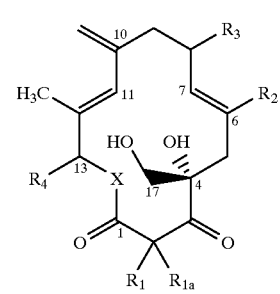

(I)

wherein $R_1$ is H or $C_1$–$C_6$ alkyl;

$R_{1a}$ is H or $C_1$–$C_6$ alkyl;

$R_2$ is H, $C_1$–$C_6$ alkyl or $C_1$–$C_6$ alkoxy;

$R_3$ is H or $C_1$–$C_6$ alkyl;

$R_4$ is H or $C_1$–$C_6$ alkyl;

X is O or NH;

with the proviso that if $R_1$ and $R_3$ are methyl and $R_{1a}$ is hydrogen, $R_4$ is ethyl and $R_2$ is methyl or methoxy, X cannot be O, or a pharmaceutically acceptable addition salt and/or hydrate thereof, or where applicable, a geometric or optical isomer or racemic mixture thereof.

2. A compound of the formula

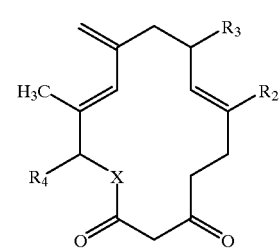

(IV)

wherein $R_2$ is H, $C_1$–$C_6$ alkyl or $C_1$–$C_6$ alkoxy;

$R_3$ is H or $C_1$–$C_6$ alkyl;

$R_4$ is H or $C_1$–$C_6$ alkyl;

X is O or NH;

or a pharmaceutically acceptable addition salt and/or hydrate thereof, or where applicable, a geometric or optical isomer or racemic mixture thereof.

3. A method of synthesizing Compound IX of the formula

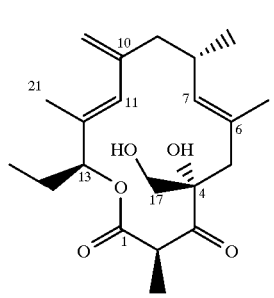

(IX)

Galbonolide B which comprises reacting Compound VI of the formula

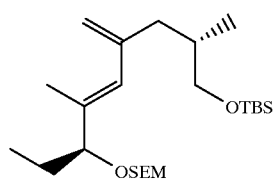

(VI)

with Compound V of the formula

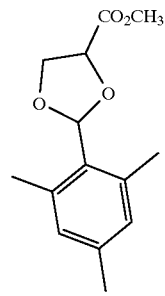

(V)

to produce Compound VII of the formula

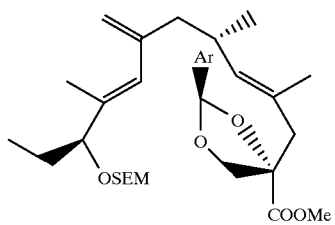

(VII)

which is subsequently converted to Compound VIII of the formula

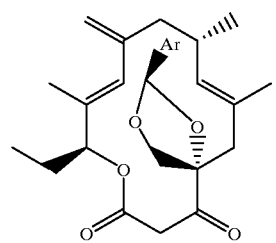

(VIII)

which is dissolved in acetic acid and water and purified to produce Compound IX.

4. An antifungal composition comprising a compound of claim 1 in admixture with a pharmaceutically acceptable carrier.

5. A method for controlling fungal infections comprising administering to a subject in need of said treatment, an antifungal amount of a compound of claim 1.

* * * * *